US010865095B2

(12) United States Patent
Scott et al.

(10) Patent No.: US 10,865,095 B2
(45) Date of Patent: Dec. 15, 2020

(54) SYSTEM AND ASSEMBLY FOR REFILLING A LIQUID RESERVOIR

(71) Applicant: Fontem Holdings 1 B.V., Amsterdam (NL)

(72) Inventors: Kenneth Scott, Lancashire (GB); Christopher Lord, Liverpool (GB); David Jones, Manchester (GB); Stephen J. McDonald, North Yorkshire (GB); Thomas S. Sudlow, Lancashire (GB)

(73) Assignee: Fontem Holdings 1 B.V.

( * ) Notice: Subject to any disclaimer, the term of this patent is extended or adjusted under 35 U.S.C. 154(b) by 334 days.

(21) Appl. No.: 15/550,726

(22) PCT Filed: Feb. 5, 2016

(86) PCT No.: PCT/GB2016/050283
§ 371 (c)(1),
(2) Date: Aug. 11, 2017

(87) PCT Pub. No.: WO2016/128718
PCT Pub. Date: Aug. 18, 2016

(65) Prior Publication Data
US 2018/0029866 A1    Feb. 1, 2018

(30) Foreign Application Priority Data
Feb. 13, 2015    (GB) .................................. 1502492.0

(51) Int. Cl.
*B67D 7/02*    (2010.01)
*A61M 11/04*    (2006.01)
(Continued)

(52) U.S. Cl.
CPC .......... *B67D 7/0294* (2013.01); *A24F 47/002* (2013.01); *A24F 47/008* (2013.01);
(Continued)

(58) Field of Classification Search
CPC ...... B67D 7/0294; B67D 7/0222; B67D 7/44; B67D 7/54; A61M 11/042; A61M 15/06;
(Continued)

(56) References Cited

U.S. PATENT DOCUMENTS 2,989,091 A  *  6/1961  Lowenthal ................ F23Q 2/52
                                                            141/294
3,094,306 A  *  6/1963  Conrad .................... E21B 34/12
                                                            251/282
(Continued)

FOREIGN PATENT DOCUMENTS

CA         2545907 A1    11/2007
CN         1436102 A      8/2003
(Continued)

OTHER PUBLICATIONS

International Search Report in WO 94/06703 (PCT/GB2016/050284) (dated Jul. 16, 2016) (6 pages).
GB Search Report in GB1502492.0 (dated Jun. 29, 2016) (6 pages).

*Primary Examiner* — Timothy L Maust
*Assistant Examiner* — James R Hakomaki
(74) *Attorney, Agent, or Firm* — Dykema Gossett PLLC

(57) ABSTRACT

The present invention relates to a system and assembly for refilling a reservoir with liquid dispensed from a dispenser, in particular, but not exclusively, to a system and assembly for the substantially leak-free refilling of the reservoir of a smoking-substitute device with a liquid comprising nicotine from a refill dispenser. The assembly is configured to provide a gas communication pathway through the assembly and physically separate from the liquid communication pathway for venting gas from an end of the assembly proximal the first aperture to an exterior of the assembly responsive to the movement of the assembly to the secured and open configuration, the assembly configured to close the
(Continued)

gas communication pathway in the unsecured and closed configuration

22 Claims, 36 Drawing Sheets

(51) Int. Cl.

| | | |
|---|---|---|
| *B05B 11/00* | (2006.01) | |
| *A24F 47/00* | (2020.01) | |
| *A61M 15/06* | (2006.01) | |
| *B65B 3/04* | (2006.01) | |
| *B65B 3/06* | (2006.01) | |
| *B65B 3/12* | (2006.01) | |
| *B65D 1/32* | (2006.01) | |
| *B65D 47/06* | (2006.01) | |
| *B65D 47/32* | (2006.01) | |
| *B67D 7/44* | (2010.01) | |
| *B67D 7/54* | (2010.01) | |
| *B65D 47/08* | (2006.01) | |

(52) U.S. Cl.
CPC .......... *A61M 11/042* (2014.02); *A61M 15/06* (2013.01); *B05B 11/0044* (2018.08); *B05B 11/0097* (2013.01); *B65B 3/04* (2013.01); *B65B 3/06* (2013.01); *B65B 3/12* (2013.01); *B65D 1/32* (2013.01); *B65D 47/06* (2013.01); *B65D 47/32* (2013.01); *B67D 7/0222* (2013.01); *B67D 7/44* (2013.01); *B67D 7/54* (2013.01); *A61M 2209/045* (2013.01); *B05B 11/0002* (2013.01); *B65D 47/0833* (2013.01)

(58) Field of Classification Search
CPC ............. B05B 11/0044; B05B 11/0097; A24F 47/002; A24F 47/008; B65B 3/04; B65B 3/06; B65B 3/12; B65D 1/32; B65D 47/06; B65D 47/32
USPC ........................................................ 141/351
See application file for complete search history.

(56) References Cited

U.S. PATENT DOCUMENTS

| | | | | |
|---|---|---|---|---|
| 3,125,135 A * | 3/1964 | Boyer | ...................... | B67D 7/54 137/587 |
| 3,217,762 A * | 11/1965 | Burchett | .................... | F23Q 2/52 141/349 |
| 3,574,314 A * | 4/1971 | Quercia | .................... | F23Q 2/52 141/349 |
| 3,590,847 A * | 7/1971 | Worden | ................ | G05D 16/106 137/116.5 |
| 3,624,755 A | 11/1971 | Lambert | | |
| 4,715,414 A * | 12/1987 | Harrison | ............... | B67D 1/0832 137/212 |
| 5,058,636 A | 10/1991 | Simmel et al. | | |
| 5,234,038 A | 8/1993 | Mitchell et al. | | |
| 5,249,611 A | 10/1993 | Law | | |
| 5,560,522 A | 10/1996 | Clark | | |
| 5,628,352 A | 5/1997 | Gracyalny et al. | | |
| 5,890,517 A | 4/1999 | Laible | | |
| 6,155,464 A | 12/2000 | Vachon | | |
| 6,322,207 B1 | 11/2001 | Hall et al. | | |
| 6,581,851 B1 | 6/2003 | Murphy | | |
| 6,637,430 B1 | 10/2003 | Voges et al. | | |
| 2004/0025968 A1 | 2/2004 | Allen | | |
| 2007/0277902 A1 | 12/2007 | Dieudonat et al. | | |
| 2010/0242975 A1 | 9/2010 | Hearn | | |
| 2012/0018036 A1* | 1/2012 | Galinha | .................. | A45D 34/06 141/20 |
| 2012/0167906 A1* | 7/2012 | Gysland | ................ | A24F 47/008 131/328 |
| 2013/0306665 A1 | 11/2013 | Eberhardt et al. | | |
| 2014/0041753 A1 | 2/2014 | Beranger et al. | | |
| 2014/0283946 A1* | 9/2014 | Kribs | ..................... | B65D 47/06 141/2 |
| 2016/0251096 A1* | 9/2016 | De Rosa | .................. | A45D 34/00 141/352 |

FOREIGN PATENT DOCUMENTS

| | | |
|---|---|---|
| CN | 1476355 A | 2/2004 |
| CN | 1933913 A | 3/2007 |
| CN | 1933915 A | 3/2007 |
| CN | 101986779 A | 3/2011 |
| CN | 102014996 A | 4/2011 |
| EP | 2500277 A1 | 9/2012 |
| EP | 3100956 A2 | 12/2016 |
| EP | 3124430 A1 | 2/2017 |
| EP | 3143884 A2 | 3/2017 |
| EP | 3254987 A1 | 12/2017 |
| EP | 3348155 A1 | 7/2018 |
| GB | 921899 A | 3/1963 |
| GB | 1579283 A | 11/1980 |
| GB | 2512326 A | 10/2014 |
| GB | 2524296 A | 9/2015 |
| GB | 2531830 B | 7/2017 |
| WO | 94/06703 A1 | 3/1994 |
| WO | 2000/017091 | 3/2000 |
| WO | 2014/195859 A2 | 12/2014 |
| WO | 2014/199098 A1 | 12/2014 |
| WO | 2015/059399 A1 | 4/2015 |
| WO | 2017024926 A1 | 2/2017 |
| WO | 2017046247 A1 | 3/2017 |
| WO | 2017071298 A1 | 5/2017 |

* cited by examiner

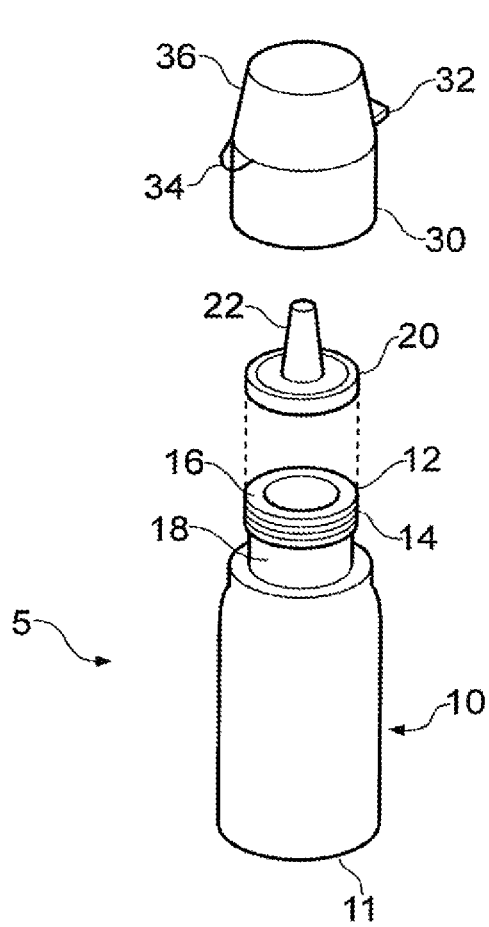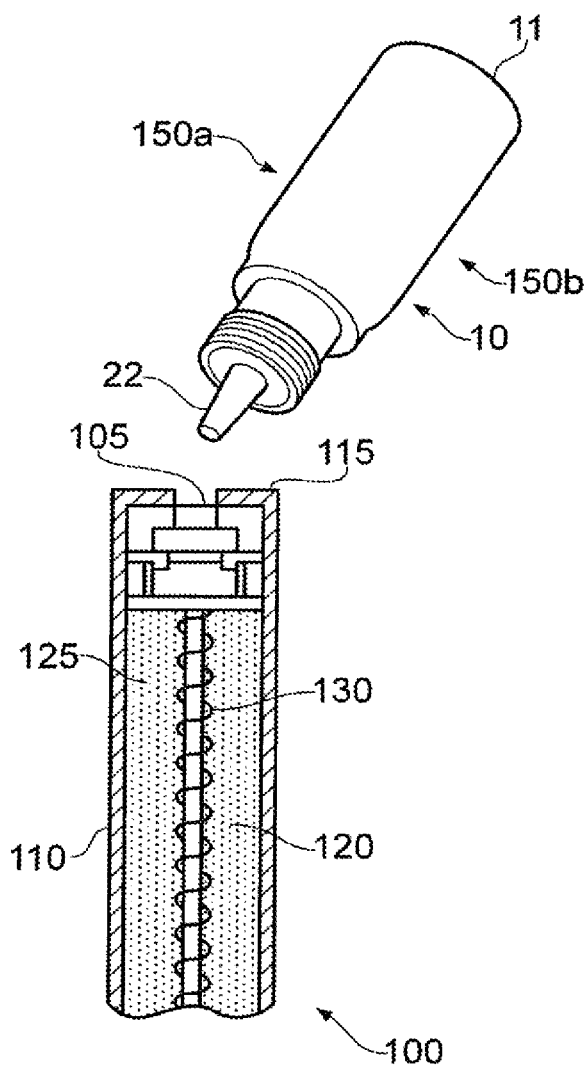
FIG. 1
Prior Art
FIG. 2
Prior Art

SYSTEM AND ASSEMBLY FOR REFILLING A LIQUID RESERVOIR

TECHNICAL FIELD

The present invention relates to a system and assembly for refilling a reservoir with liquid dispensed from a dispenser, in particular, but not exclusively, to a system and assembly for the substantially leak-free refilling of the reservoir of a smoking-substitute device with a liquid comprising nicotine from a refill dispenser.

BACKGROUND

A smoking-substitute device is an electronic device that permits the user to simulate the act of smoking by producing an aerosol mist or vapour that is drawn into the lungs through the mouth and then exhaled. The inhaled aerosol mist or vapour typically bears nicotine and/or other flavourings without the odour and health risks associated with traditional smoking and tobacco products. In use, the user experiences a similar satisfaction and physical sensation to those experienced from a traditional smoking or tobacco product, and exhales an aerosol mist or vapour of similar appearance to the smoke exhaled when using such traditional smoking or tobacco products.

A smoking-substitute device generally uses heat and/or ultrasonic agitation to vaporize a solution comprising nicotine and/or other flavouring, propylene glycol and/or glycerine-based base into an aerosol mist of vapour for inhalation. A person of ordinary skill in the art will appreciate that the term "smoking-substitute device" as used herein includes, but is not limited to, electronic nicotine delivery systems (ENDS), electronic cigarettes, e-cigarettes, e-cigs, vaping cigarettes, pipes, cigars, cigarillos, vaporizers and devices of a similar nature that function to produce an aerosol mist or vapour that is inhaled by a user. Such smoking-substitute devices incorporate a liquid reservoir element generally including a vaporizer or misting element such as a heating element or other suitable element, and are known inter alia, as atomizers, cartomizers and clearomizers. Some electronic cigarettes are disposable; others are reusable, with replaceable and refillable parts.

Smoking-substitute devices typically resemble a traditional cigarette and are cylindrical in form with a mouthpiece at one end through which the user can draw the aerosol mist or vapour for inhalation. These devices usually share several common components: a power source such as a battery, a reservoir for holding the liquid to be vaporized, a vaporization component for atomizing and/or vaporizing the liquid and to thereby produce an aerosol mist and/or vapour, and control circuitry operable to actuate the vaporization component responsive to an actuation signal from a switch operative by a user or configured to detect when the user draws air through the mouthpiece by sucking or inhaling.

The reservoir may be either a replaceable or refillable container that is coupled to, or located in, the main body of the smoking-substitute device and that is typically made of a resilient plastic material such as high-density polypropylene. The reservoir generally contains a wicking material in which the liquid is stored but may just be a storage space without any wicking material. Once the replaceable or refillable reservoir is emptied it must either be replaced or refilled.

Replaceable type reservoirs are typically provided in the form of a pre-filled cartridge that can be securely and removably engaged to, or within, the cylindrical main body of the smoking-substitute device. These reservoir and vaporization elements may also be integrated into a single component commonly known as a "cartomizer" that may be disposable or refillable. Additionally, replaceable type reservoirs may also be integrally formed with the mouthpiece.

In order to fit a replaceable type reservoir to, or within, the main body of a smoking-substitute device, features of the main body are configured to engage with complementary features formed on a portion of the reservoir to securely and removably couple the reservoir to the main body of the smoking substitute device and to thereby prevent the accidental or unintended separation of the reservoir from the smoking-substitute device. These complementary features typically secure the reservoir to the main body of the smoking-substitute device with a close or interference fit and the fitting step causes a portion of the main body of the smoking-substitute device to pierce the reservoir to permit liquid to be dispensed.

Alternatively, and most commonly, users utilise refillable type reservoirs. Typically, the refillable reservoir of the smoking-substitute device is refilled by dispensing liquid from a dispenser that commonly resembles the small dropper bottles used for dispensing eye drops. Refill dispensers are preferred principally for their low cost.

The ingredients of the liquid for producing the aerosol mist or vapour in smoking-substitute devices vary widely, but typically include water and flavourings in a propylene glycol and/or glycerol base. Nicotine may also be included in solutions intended to fulfil a nicotine replacement role, without the harmful products associated with tobacco smoke.

A person of ordinary skill in the art will appreciate that the term "liquid" as used herein, may include, but is not limited to, any liquids, gels, powders and gases together with liquids comprising mixtures of liquids, gels, powders and gases that are capable of being atomized or vaporized whether or not using heat and/or ultrasonics.

When refilling the reservoir from a dispenser, the user typically drips liquid from the outlet liquid-dispensing tip of the dispenser into an inlet of the reservoir by squeezing the walls of the dispenser. Any wicking material in the reservoir then absorbs the dispensed liquid or the space in the reservoir is simply filled with the dispensed liquid. Since the diameter of the inlet on the smoking-substitute device is typically quite narrow it is important that the liquid-dispensing tip of the dispenser is correctly aligned to prevent spillage. Additionally, the user must correctly judge the pressure with which the dispenser should be squeezed to controllably expel liquid from the liquid-dispensing tip. Furthermore, as the user releases the bottle air is sucked in through the liquid-dispensing tip to replace the volume of liquid that has just been dispensed, but can also suck recently dispensed liquid from the reservoir and back into the dispenser causing droplets of liquid to be expelled inadvertently from the reservoir. Consequently, this refill technique is cumbersome and typically results in spillages of oily liquid, which has an oily consistency, and so some users have found that utilizing a syringe to draw liquid from the outlet of the dispenser before injecting it through the inlet of the reservoir is more convenient.

A method of refilling the reservoir of a smoking-substitute device from a dispenser is disclosed in US 2014/0283946 A1 (Kribs, et al). This published patent application describes a cap that fits over the liquid-dispensing tip of a standard eyedropper type refill dispenser. The cap has a first portion with a bore into which the liquid-dispensing tip of a standard bottle is received, and an inner annular wall that is threaded, such that a gap is disposed between the liquid-dispensing tip and the threaded portion of the inner annular wall. When liquid is to be dispensed into the reservoir to refill the reservoir, the first portion of the cap is screwed onto a reciprocal threaded outer portion of the smoking-substitute device. When fully engaged the first portion of the cap is substantially sealed against the inlet of the reservoir of the smoking-substitute device to permit liquid to flow between the dispenser and the reservoir and alleviate leakage.

The popularity and use of smoking-substitute devices has grown rapidly in the past few years. Although originally marketed as an aid to assist habitual smokers wishing to quit traditional smoking and tobacco products, consumers are increasingly viewing smoking substitute devices as desirable lifestyle accessories. This has caused concern that smoking-substitute devices may be becoming fashionable in certain sections of the population, and that their use may as a consequence be attractive to children and young adults who may subsequently graduate to traditional smoking and tobacco products.

There is also significant on-going scientific debate about the long-terms effects on health from the prolonged use of smoking-substitute devices and the inhalation of atomized mists and/or vapours comprising nicotine constituents. However, it is generally accepted that the levels of toxicants consumed by users of such smoking-substitute devices is a fraction of those consumed by users of traditional smoking and tobacco products. See, for example, John H. Lauterbach et al, "Suggested Protocol for Estimation of Harmful and Potentially Harmful Constituents in Mainstream Aerosols generated by Electronic Delivery Systems (ENDS)", presented at SOT, San Francisco, Calif., Mar. 10-16, 2012 and hereby incorporated by reference.

Nonetheless, the health issues connected with the prolonged use of smoking-substitute devices is increasingly receiving negative press coverage and is the subject of much political debate. One area of particular concern is the quality and provenance of many liquids presently available on the market. Concerns raised, particularly by the medical profession, also focus on the lack of information available to consumers regarding the use of smoking-substitute devices and associated liquids that prevent them from making informed decisions regarding their use.

To address safety and quality concerns relating to traditional smoking and tobacco products, the World Health Organisation (WHO) published the Framework Convention on Tobacco Control (FCTC) in May 2003. The FCTC provisions are intended to regulate the sale and marketing of tobacco and tobacco-alternative products, the disclosure of information relating to such products, the packaging and labelling of such products, and the advertising of such products. These provisions are binding on the European Union (EU) and its' Member States who have adopted a set of guidelines for the implementation of the FCTC provisions by consensus during a series of subsequent conferences. Although, the FCTC did not anticipate the market for smoking-substitute devices, the governments of several Member States have decided that it would be appropriate to adapt the current legislation resulting from the FCTC and that relates to traditional smoking and tobacco products to incorporate such smoking-substitute devices.

In Europe efforts to adapt the existing legislation followed the publication of various reports and advice received from the Scientific Committee on Newly Identified Health Risks (SCENIHR) on smokeless tobacco products and tobacco additives. The European Parliament and Council of the European Union has proposed repealing Directive 2001/37/ EC and replacing it with Directive 2014/40/EU on Apr. 3, 2014 (Tobacco Products Directive or TPD). Although still to be enacted into the national laws of the Member States of the EU and not expected to come into force until May 2016, the TPD proposes regulations applicable to smoking-substitute devices that will:

limit the risks of inadvertent exposure to nicotine by setting maximum sizes for refill reservoirs, containers, tanks, and cartridges (Article 20.3(a))

limit the concentration of nicotine in the liquid to 20 mg/ml (Article 20.3(b)).

prohibit the use of certain additives in the liquid (Article 20.3(c))

require that only high-purity ingredients are used in the manufacture of liquids (Article 20.3(d)).

require that all ingredients (except nicotine) do not pose a risk to human health in heated or unheated form (Article 20.3(e))

require that all smoking-substitute devices deliver doses of nicotine at consistent levels under normal conditions of use (Article 20.3(f))

require that all products include child and tamper-proof labelling, fasteners and opening mechanisms (Article 20.3(g)).

require that all products meet certain safety and quality standards and to ensure that products do no break or leak during use or refill (penultimate and final sentences, paragraph 41 of the recitals).

One area of particular concern to consumers and regulators is that the increased availability of smoking-substitute devices and refill liquids in supermarkets and other outlets may create a health risk particularly if they fall into the hands of children. Although these liquids typically comprise nicotine in concentrations of less than or equal to 3.6% of the liquid which is generally regarded as safe and merely a stimulant, Nicotine in much higher concentration has in the past been used as an insecticide and in concentrations of 50-100 mg can be harmful to humans. Nonetheless, solutions comprising nicotine are treated as toxic by postal services and carriers, and so appropriate precautions are required when handling and storing nicotine in bulk.

Aspects and embodiments of the invention were devised with the foregoing in mind.

BRIEF SUMMARY OF THE PRESENT INVENTION

The present invention seeks to address at least one of the problems of the prior art by providing a system and assembly for readily refilling the reservoir of a smoking-substitute device with liquid from a dispenser. The system and assembly in accordance with aspects of the present invention prevents liquid from being dispensed until the dispenser is sealably engaged to the smoking-substitute device and may substantially alleviate the problems of spillage and/or leakage when dispensing liquid from the dispenser into the reservoir of the smoking-substitute device.

According to an aspect of the present invention, there is provided an assembly for controllably transferring liquid therethrough, the assembly moveable between an unsecured and closed configuration in which liquid communication is restricted between a first and a second aperture disposed at respective ends of the assembly, and a secured and open configuration in which an openable liquid communication pathway between the first and the second aperture is opened; wherein the assembly is configured to provide a gas communication pathway through the assembly and physically separate from the liquid communication pathway for venting gas from an end of the assembly proximal the first aperture to an exterior of the assembly responsive to the movement of the assembly to the secured and open configuration, the assembly configured to close the gas communication pathway in the unsecured and closed configuration.

Physical or mechanical separation of gas and liquid communication pathways in the assembly may allow an ambient pressure to be maintained in a reservoir being filled using the assembly. Further, leakage of liquid from the liquid communication pathway to the gas communication pathway may be inhibited.

Optionally, the gas communication pathway may be configured to vent gas to an exterior of the assembly concomitant with movement of the assembly between the closed and the open configurations. Further optionally. the gas communication pathway may be configured to vent to atmosphere.

The gas communication pathway may be configured to inhibit the passage of a liquid therethrough and, optionally, may be configured to inhibit capillary motion of a liquid from the reservoir through the gas communication pathway. Further optionally, the gas communication pathway may comprise one or more convolutions. Yet further optionally, the gas communication pathway may be configured in the form of a tesla valvular conduit for preferential flow of liquid against the direction of gas flow from the reservoir.

The assembly may be configured to close both the liquid communication pathway and the gas communication pathway responsive to movement away from the secured position.

Optionally, in the open position, the assembly may be operable to permit liquid to be transferred through the liquid communication pathway, and for a substantially equivalent volume of gas to be expelled through the gas communication pathway.

Optionally, the assembly may be biased towards the closed position and, further optionally, the bias may be a resilient bias.

The assembly may further comprise a first valve arrangement for opening and closing the liquid communications pathway and a second valve arrangement operatively coupled to the first valve arrangement to open and close said gas communications pathway responsive to said movement of said assembly to said secured and open configuration. Optionally, the first and second valve arrangements may be biased shut when the coupling assembly is not secured in the open position.

Optionally, the assembly may further comprise: a reservoir portion configured for securely coupling to a liquid reservoir inlet; a dispenser portion connected to the reservoir portion and configured for securely coupling to a liquid dispenser outlet; and the reservoir portion and dispenser portion configured to cooperatively combine to form the liquid communication pathway. Further optionally, the reservoir portion may comprise a first closure member and the dispenser portion may comprise a second closure member for closing the liquid communications pathway, the first and second closure members seated in respective first and second closeable apertures in the unsecured and closed configuration and movable from the seated position between to the secured and open configuration to open the liquid communications pathway. Yet further optionally, the first closure member and the second closure member may be configured to abut one another to effect movement of the first and second closure members from the first and second closeable apertures responsive to an actuation force applied to a one or more of the first and second closure members.

Optionally, movement of the first and second closure members from the first and second closeable apertures may be against the bias.

Optionally, the reservoir portion may comprise first and second components configured to cooperatively define a gas channel open at an end proximal the first aperture and extending to an end distal the first aperture, the first and second components movable with respect to each other to open the distal end of the gas channel; and the dispenser portion may comprise a third component movable with respect to the first component to act on the second component to move the first and second components with respect to each other concomitant with movement of the assembly from the non-dispensing configuration to the dispensing configuration to expose the distal end of the gas channel to provide the gas communication pathway to an exterior of the assembly. Further optionally, the third component may be configured to provide a second gas channel including an end configured to open to the distal end of the gas channel to provide the gas communication pathway to an exterior of the assembly responsive to movement of the first and second component with respect to each other under actuation of the third component. Yet further optionally, an inner wall of the second component and an outer wall of the third component may be configured to cooperate to provide the second gas channel.

Optionally, the outer wall of the third component may comprise a groove extending lengthwise from an end region of the third component distal the second aperture. Further optionally, the reservoir portion and the dispenser portions may cooperate to form another groove between an inner wall of the first component and an outer wall of the second component to provide the gas channel and wherein movement of the first and second component under actuation of the third component opens a side of the other groove to a side of the groove to provide the gas communication pathway.

Optionally, the assembly may further comprise mutually complementary interengagement formations disposed on the reservoir portion and the dispenser portion and configured to securely engage the reservoir portion to the dispenser portion in the secured and open configuration. Further optionally, the mutually complementary interengagement formations may be configured to guide movement of the reservoir portion and dispenser portion members with respect to each other to move the first and second closure members from the closed and unsecured position to the open and secured position.

Optionally, the first closure and first closeable aperture and the second closure and the second closeable aperture form the first valve arrangement.

Optionally, the gas channel and the second gas channel may form the second valve arrangement.

Optionally, the assembly may further comprise a male member, and a female member configured for securely and removably receiving the male member.

Optionally, the assembly may be configured for sealably cooperating with a reservoir of a smoking-substitute device. Further optionally, the assembly may be configured for cooperating with the reservoir of a smoking-substitute device.

Various optional configurations of the assembly may be suitable, including a bayonet-type arrangement, a magnetic-type arrangement, a screw-type arrangement, a slide-type arrangement, a friction-fit-type arrangement, and a speed-fit type arrangement.

According to another aspect of the present invention, there is provided a reservoir portion for the assembly as described above and hereinafter.

According to another aspect of the present invention, there is provided a dispenser portion for the assembly as described above and hereinafter.

According to another aspect of the present invention, there is provided a reservoir portion for controlling the ingress of liquid into the reservoir portion and the egress of gas from the reservoir portion, the reservoir portion comprising an first openable aperture for providing a liquid pathway for the ingress of a liquid into the reservoir portion and second openable aperture for providing a gas pathway for the egress of gas from the reservoir portion, wherein the liquid pathway and the gas pathway are physically separate from each other within the reservoir portion According to another aspect of the present invention, there is provided a dispenser for dispensing a liquid, the dispenser configured to cooperate with the assembly as described above and hereinafter. Optionally, the dispenser may be configured to be securely coupled to the assembly.

According to another aspect of the present invention, there is provided a reservoir for receiving and storing liquid, the reservoir configured to cooperate with the assembly as described above and hereinafter to receive liquid through the assembly.

According to another aspect of the present invention, there is provided a system for transferring liquid between a dispenser and a reservoir, comprising: an assembly an assembly, as described above and hereinafter; a dispenser, as described above and hereinafter; and a reservoir, as described above and hereinafter.

According to another aspect of the present invention, there is provided a smoking-substitute device comprising a reservoir as described above and hereinafter. Optionally, the reservoir may be removable from the device. Optionally, the reservoir may be integral with the device.

The features, advantages and benefits of embodiments of the present invention will be more fully understood and appreciated upon consideration of the following detailed description and accompanying drawings, which set forth illustrative embodiments in which the concepts of the invention are utilized.

BRIEF DESCRIPTION OF THE DRAWINGS

A complete understanding of the present invention may be obtained by reference to the accompanying drawings, when considered in conjunction with the subsequent, detailed description, provided by way of example only and in which:

FIG. 1 is an exploded perspective view illustration showing a prior art liquid dispenser of the type typically used for refilling the reservoir of a smoking-substitute device;

FIG. 2 is an exploded perspective view illustration showing a liquid dispenser of the type described in connection with FIG. 1 being used to dispense liquid into the reservoir of a smoking-substitute device;

DETAILED DESCRIPTION OF THE INVENTION

Figure 3:
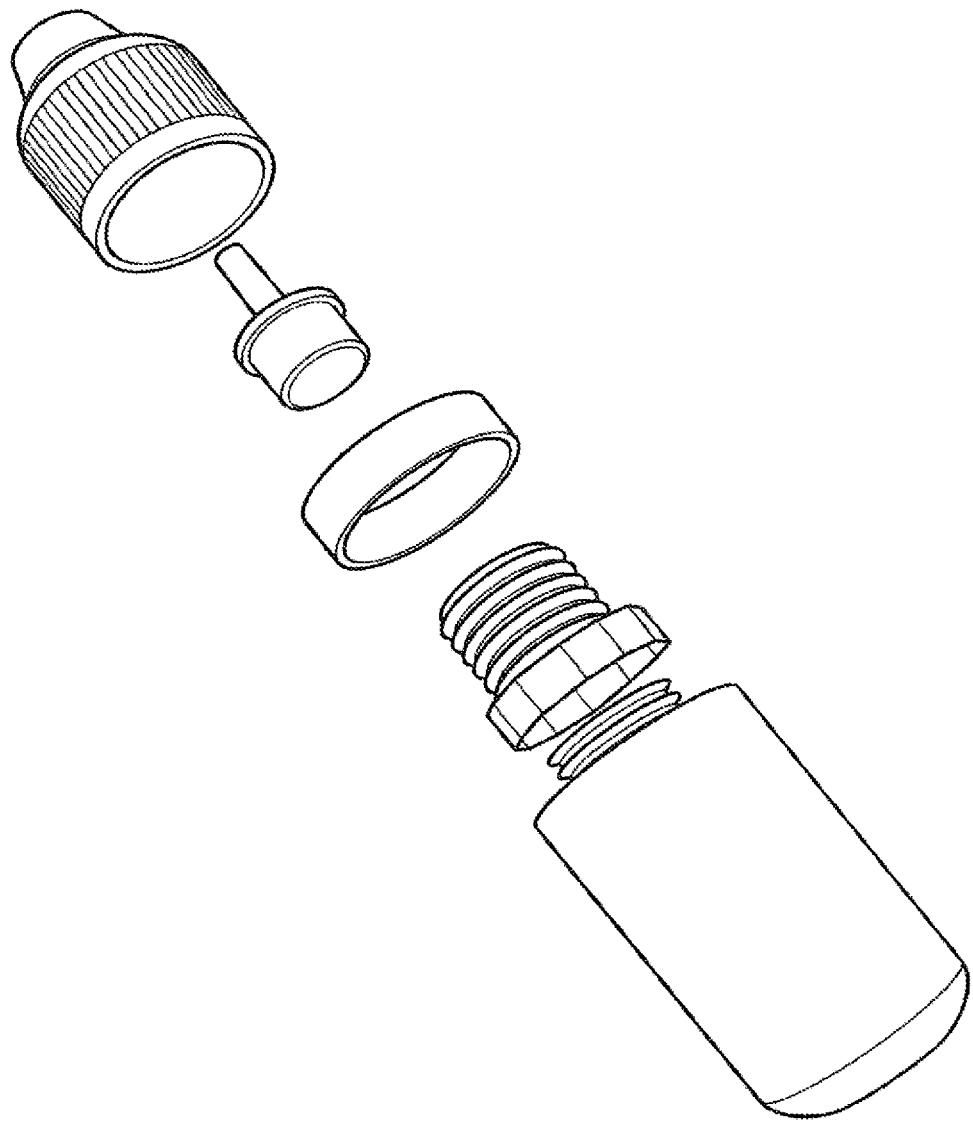
FIG. 3 is a schematic exploded view illustration of a prior art dispenser bottle.

Before the invention is described in further detail, it is to be understood that the invention is not limited to the particular embodiments described, as such may, of course, vary. It is also to be understood that the terminology used herein is for the purpose of describing particular embodiments only, and not intended to be limiting, since the scope of the present invention will be limited only by the appended claims.

Unless defined otherwise, all technical and scientific terms used herein have the same meaning as commonly understood by one of ordinary skill in the art to which this invention belongs or as determined by the context in which they are used. Although any methods and materials similar or equivalent to those described herein can also be used in the practice or testing of the present invention, a limited number of the exemplary methods and materials are described herein.

It must also be noted that as used herein and in the appended claims, the singular forms "a", "an", and "the" include plural referents unless the context clearly dictates otherwise.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, if dates of publication are provided, they may be different from the actual publication dates and may need to be confirmed independently.

The disclosure herein is directed to systems and apparatus for refilling a liquid reservoir from a refill dispenser and has particular applicability to the filling and refilling of the refillable reservoirs of smoking-substitute devices.

FIG. 1 shows an eyedropper type liquid dispenser 5 of the type presently used for refilling smoking-substitute devices. The liquid dispenser 5 includes a container 10, a dispensing portion 20 that comprises a liquid-dispensing tip 22, and a cap portion 30 that may be integrally formed with the neck portion 18 of the dispenser 10, the dispensing portion 20, or removable. As illustrated in FIG. 1, the cap portion 30 is removable and has a hinged portion 32 for permitting the lid portion 36 to be opened about the hinge portion 32 to expose the liquid-dispensing tip 22. Also illustrated is projection 34 which is provided to facilitate easy opening of the lid portion 36 by the user and when in the closed position prevents leakage from the liquid-dispensing tip 22.

Referring now to FIG. 2, a liquid dispenser 10 of the type described in relation to FIG. 1 is shown, together with a cross-sectional view of a portion of the body 110 of a smoking-substitute device 100 in which a reservoir 120 is located. The smoking-substitute device illustrated in FIG. 2 is of the type where access to the reservoir 120 is afforded by removing the mouthpiece (not shown) and the reservoir 120 is integrally formed with the vaporization chamber. Thus, the reservoir 120 is typically located in the proximal end 115 to the mouthpiece (not shown) and comprises a coiled heating element 130.

The reservoir 120 contains wicking material 125 for holding the liquid. The outer walls of the reservoir 120 are typically formed from a plastic material such as high-density polypropylene.

Before attempting to refill the smoking-substitute device the user must first remove the mouthpiece to provide access to the inlet aperture 105 of the reservoir 120. The user typically holds the smoking-substitute in an orientation in which its proximal end (i.e. the mouthpiece end) is uppermost. Although the smoking-device does not necessarily need to be vertical and slight inclination is possible to facilitate refilling, and indeed slight inclination can aid refilling, angles greater than around 20 degrees from the vertical can result in spillage.

Refill dispenser 10 is shown held at an angle of approximately 45 degrees from the vertical with the liquid-dispensing tip 22 disposed in the vicinity of the inlet aperture 105 of the smoking-substitute device so that any droplets expelled therefrom would fall generally in the region of such inlet aperture 105. Users typically find refilling of the reservoir 120 of a smoking-substitute device to be easier if the dispenser is held at an angle as their view of the liquid-dispensing tip 22 is not restricted by the body of the dispenser 10.

In use, the user will hold the refill dispenser 10 in an inverted orientation and a droplet of liquid typically forms at the end of the liquid-dispensing tip 22. Any volume in the body of the dispenser 10 that is not filled with liquid is typically air, which naturally rises to the bottom 11 of the dispenser 10 when it is disposed in a substantially inverted orientation. To dispense liquid from the tip 22 the user squeezes the body of the dispenser 10 by applying pressure in the direction of arrows 150a and 150b causing the liquid to be expelled from the end of the tip 22. Furthermore, the walls of the dispenser 10 in the region adjacent the arrows 150a and 150b may be inwardly deformed resulting in a reduction of the internal volume of the dispenser 10. Since the dispenser 10 is typically moulded from a resilient plastic material, as the user releases the inwardly directed pressure applied to the walls of the dispenser 10 they return to their normal position. Consequently, as a volume of liquid has been dispensed from the dispenser 10 into the reservoir 120 the vacant volume will be replaced with air drawn through the tip 22.

Figure 4:
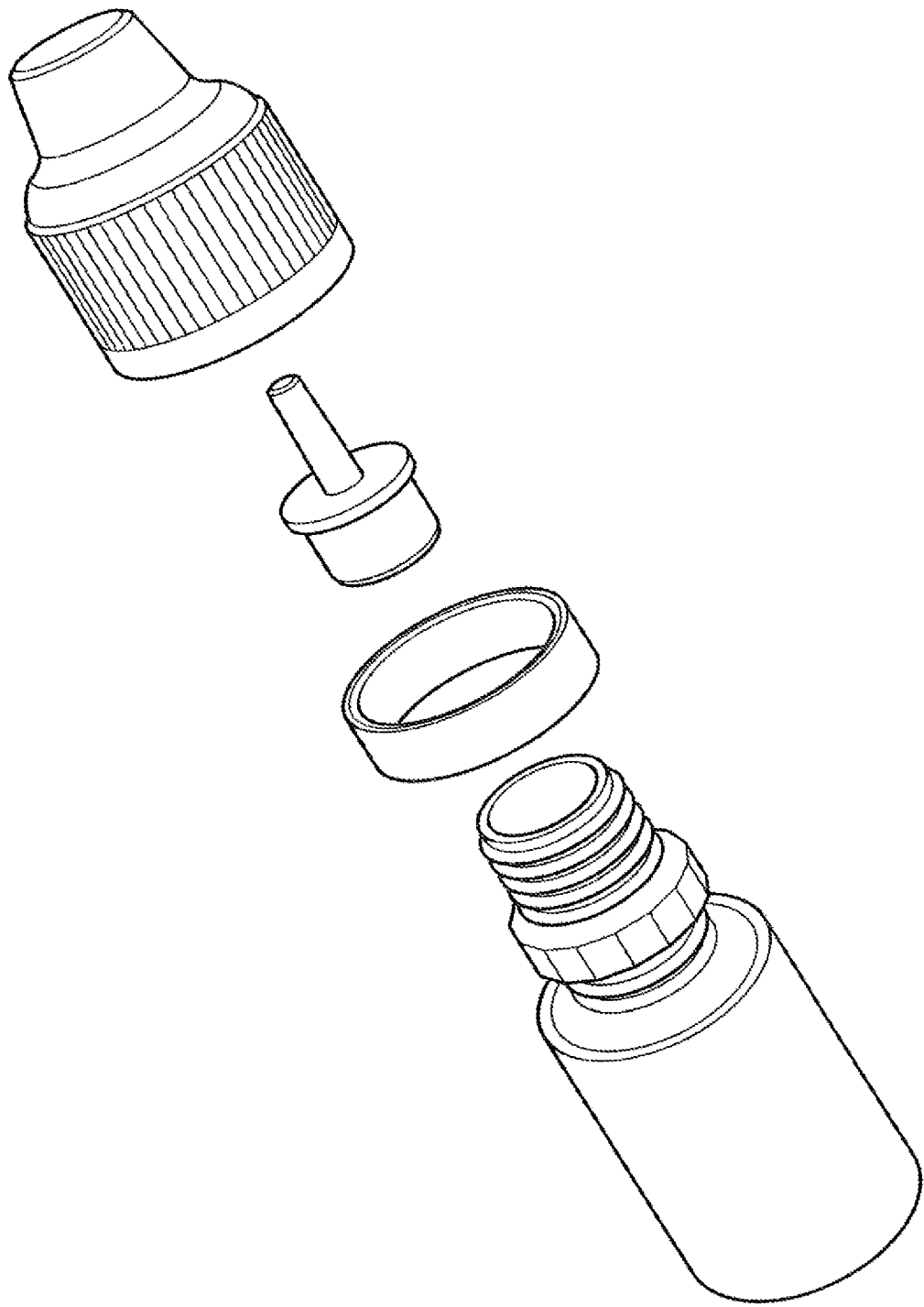
FIG. 4 is a schematic exploded view illustration of another prior art dispenser bottle.
Figure 5:
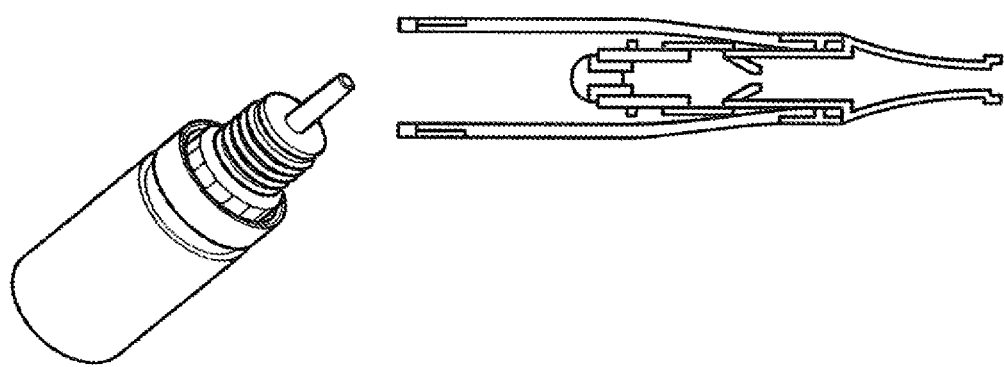
FIG. 5 is a cross-section view of a known e-cigarette being filled from a dispenser bottle.

Other known dispensers are illustrated in FIGS. 3 and 4. FIG. 5 illustrates in cross-section a known e-cigarette being filled from a dispenser bottle.

Figure 6:
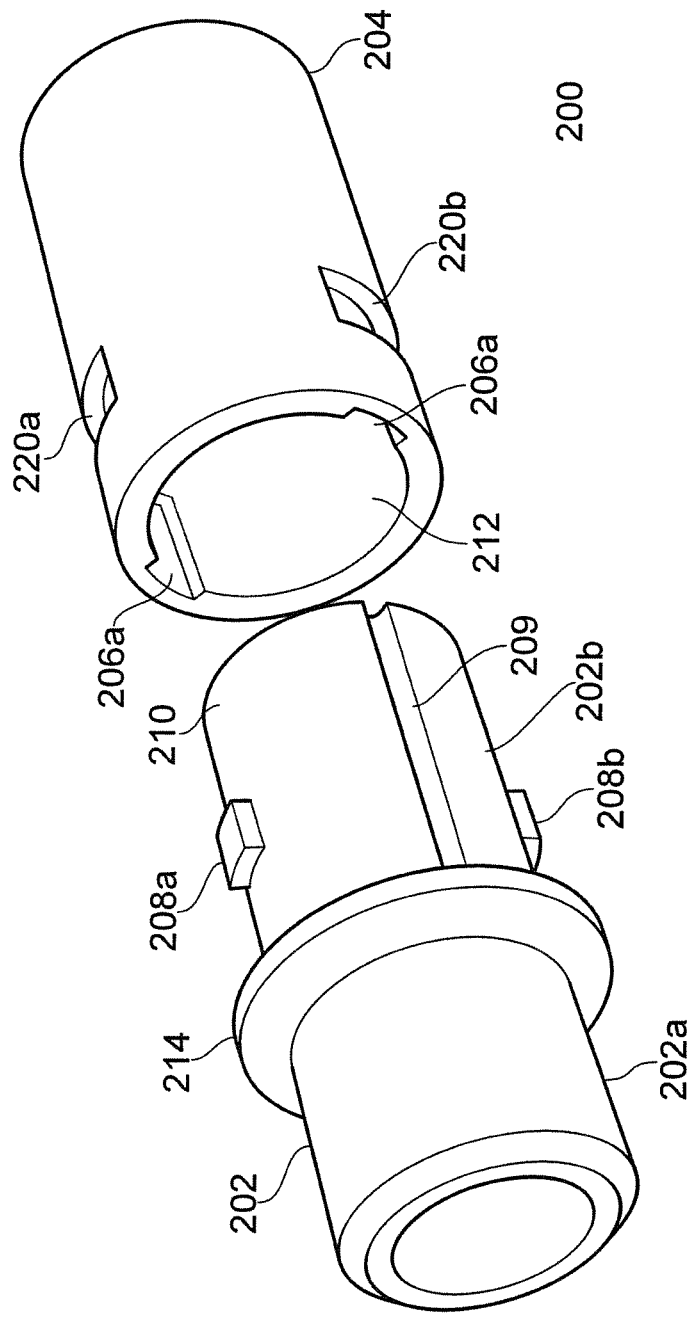
FIG. 6 is a perspective view illustration of the main features of the male and female components of apparatus in accordance with an aspect of the present invention.

Turning now to FIG. 6, a perspective view of a disengaged coupling assembly 200 in accordance with an embodiment of the present invention is illustrated. The assembly comprises two main components, a male component 202 and a female component 204. The female component 204 forms a hollow cylinder and has grooves 206a and 206b formed in the interior wall of the cylinder. The grooves 206a and 206b are configured to receive tongues 208a and 208b respectively and grooves 206 and tongues 208 cooperate to guide the male component 202 into engagement with the female component 204 through cavity 212. The exterior wall 362 of plunger guide 210 of the male component 202 is slideably engaged with the interior wall of the hollow cylinder forming the female component 204 other than in the region of wall 210 comprising groove 209.

The male component 202 comprises a flange 214 formed to provide a convenient abutment of two parts, 202a and 202b, of the male component 202 which are manufactured as separate units to allow for assembly of the other elements of the male components 202 as will be evident from the later description.

The female component 204 also includes slots 220a and 220b which are in respective communication with grooves 206a and 206b to receive tongues 208a and 208b respectively. Slots 220 extend in a circumferential direction and are shaped to provide a locking function by having a barrier around which a tongue may be moved against a bias. When the tongue has been moved around the barrier the bias returns it to a position in the slot such that the barrier inhibits the tongue returning back through the slot thereby inhibiting a twisting or rotational motion of the male and female components one with respect to the other.

Figure 7:
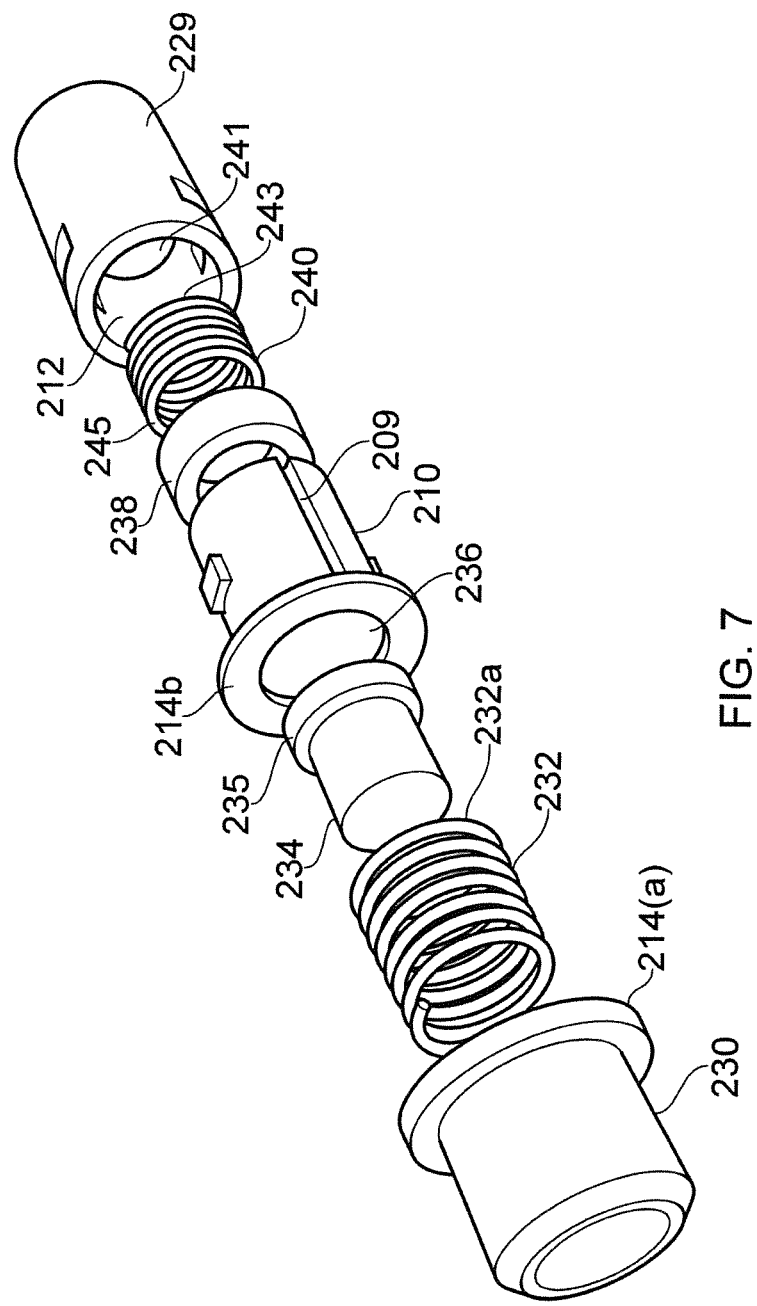
FIG. 7 is an exploded perspective view illustration showing the male and female components of apparatus in accordance with an aspect of the present invention.

Referring now to FIG. 7, the two part configuration of male component 202 is clearly illustrated and comprises plunger guide 210 and an end cap 230. The plunger guide 210 has a flange 214b and end cap 230 has a flange 214a which facilitates joining respective parts, plunger guide 210 and end cap 230, together. A helical coil spring 232 is inserted into the end cap 230 and a plunger 234 extends through the middle of helical coil spring 232 so that a shoulder 235 on the plunger 234 may contact end 232a of the spring 232. The plunger 234 is inserted into the hollow cylindrical cavity 236 of part 210 of the male component. The respective parts of male component 202 may then be assembled.

Female component 204 comprises a main hollow cylinder 229, a collar 238 and second helical coil spring 240. The collar 238 and spring 240 are slideably insertable into the cavity 212 of the hollow cylinder 229 of the female component 204. A stopper 241 protrudes from an end of cylinder 229 distal from the end into which the spring 240 and collar 238 are inserted into the cylinder 229. The spring fits around stopper 241 and the distal end, 243, of the spring engages with an end wall (not shown) of the cylinder 229 of the female component 204. The proximal end, 245, of spring 240 engages with collar 238.

Figure 8:
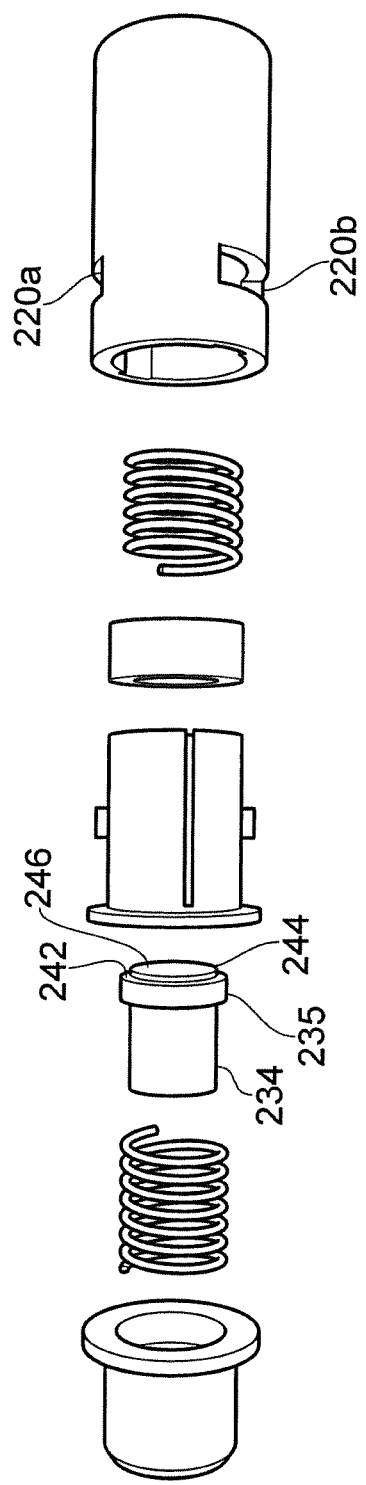
FIG. 8 is an exploded perspective view illustration showing the male and female components of apparatus in accordance with an aspect of the present invention from a different perspective.

FIG. 8 is an illustration of an exploded view of the assembly from another perspective showing plunger 234 and details of the shoulder 235. Shoulder 235 includes an engagement surface 242, a neck 244 extending from the engagement surface and plunger head 246.

Figure 9:
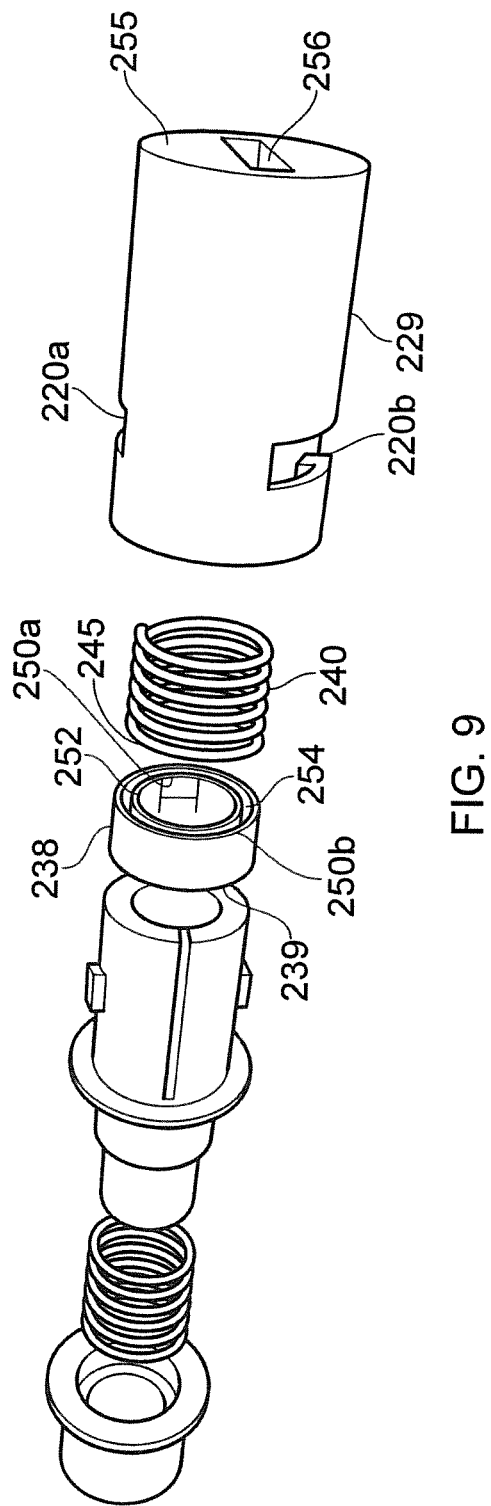
FIG. 9 is an exploded perspective view illustration showing the male and female components of apparatus in accordance with an aspect of the present invention from a further different perspective.

An exploded view of the assembly from a yet another perspective is illustrated in FIG. 9 and shows details of collar 238. Collar 238 comprises a cylindrical groove 254 which on an inner wall 252 supports diametrically opposed catch members 250a and 250b. Distal end 245 of spring 240 is configured to be insertable into groove 254 and abut against the end wall 239 of collar 238. Hollow cylinder 229 is also shown having an end wall 255 with a cavity 256 which forms a pathway for liquid into the interior of cylinder 229.

Figure 10:
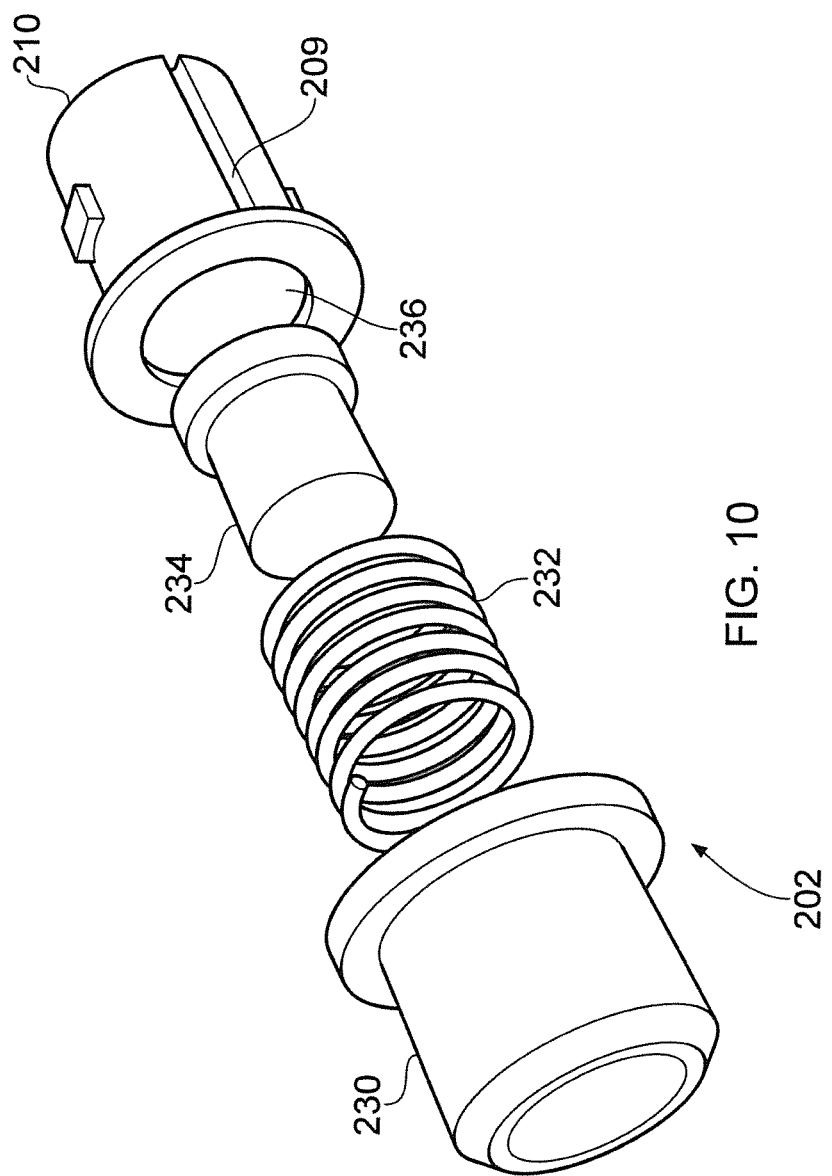
FIG. 10 is a perspective view illustration showing the male component of apparatus in accordance with an aspect of the present invention.
Figure 11:
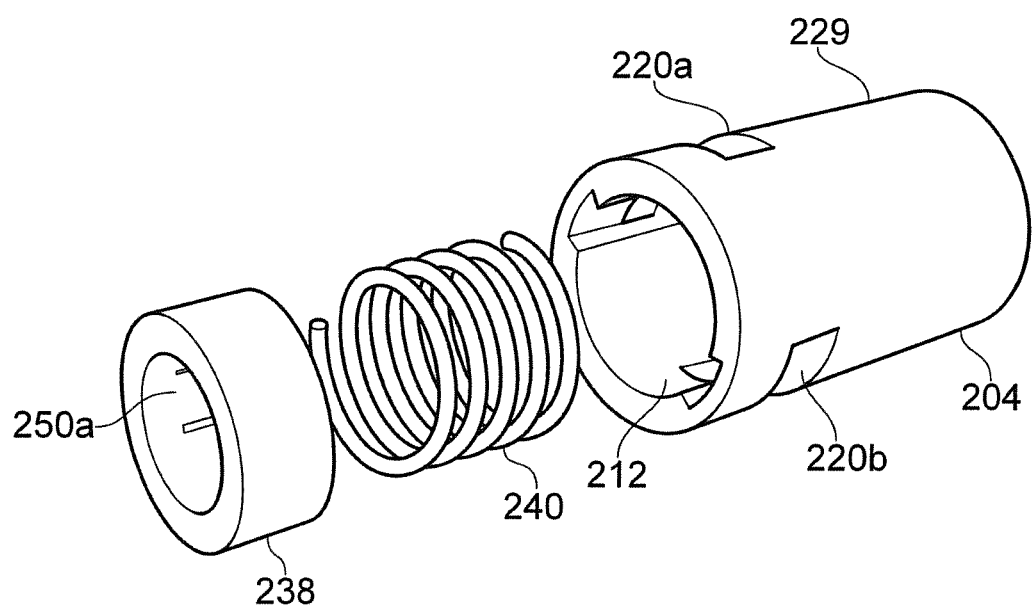
FIG. 11 is an exploded perspective view illustration showing the female component of apparatus in accordance with an aspect of the present invention.

FIG. 10 is a simple illustration showing that plunger 234 fits into the middle of spring 232 which itself fits into end cap 230. Plunger 234 is also shown as fitting into the cavity 236 of plunger guide 210 of the male component 202. Likewise, FIG. 11 is a simple illustration which in this case shows that spring 240 fits into cavity 212 of the cylinder 229 of female component 204 and collar 238 fits over the end of spring 240 and into cavity 212. A catch member 250a is also partially visible in the figure.

Figure 12:
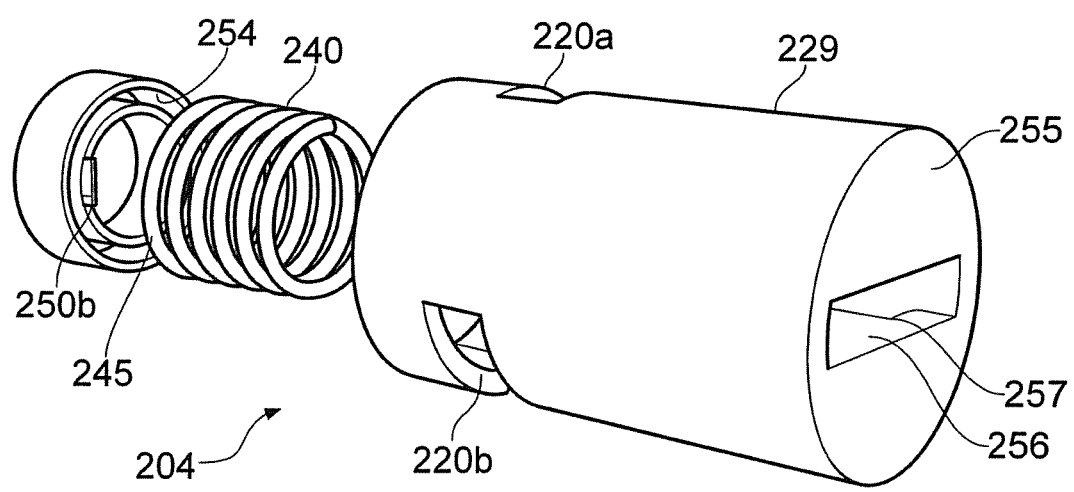
FIG. 12 is an exploded perspective view illustration showing the female component of apparatus in accordance with an aspect of the present invention from a different perspective.

FIG. 12 illustrates the female component 204 from another perspective clearly showing that the distal end 245 of spring 240 fits into groove 254. Catch member 250b is also partially visible. Also visible is end wall 255 and cavity 256. Also partially visible is a strut 257 which extends from end wall 255 to support stopper 241 (not shown). As can be seen, strut 257 does not extend to the inner side wall of cylinder 229 thereby providing a pathway for liquid from the interior of cylinder 229 to cavity 256.

Figure 13:
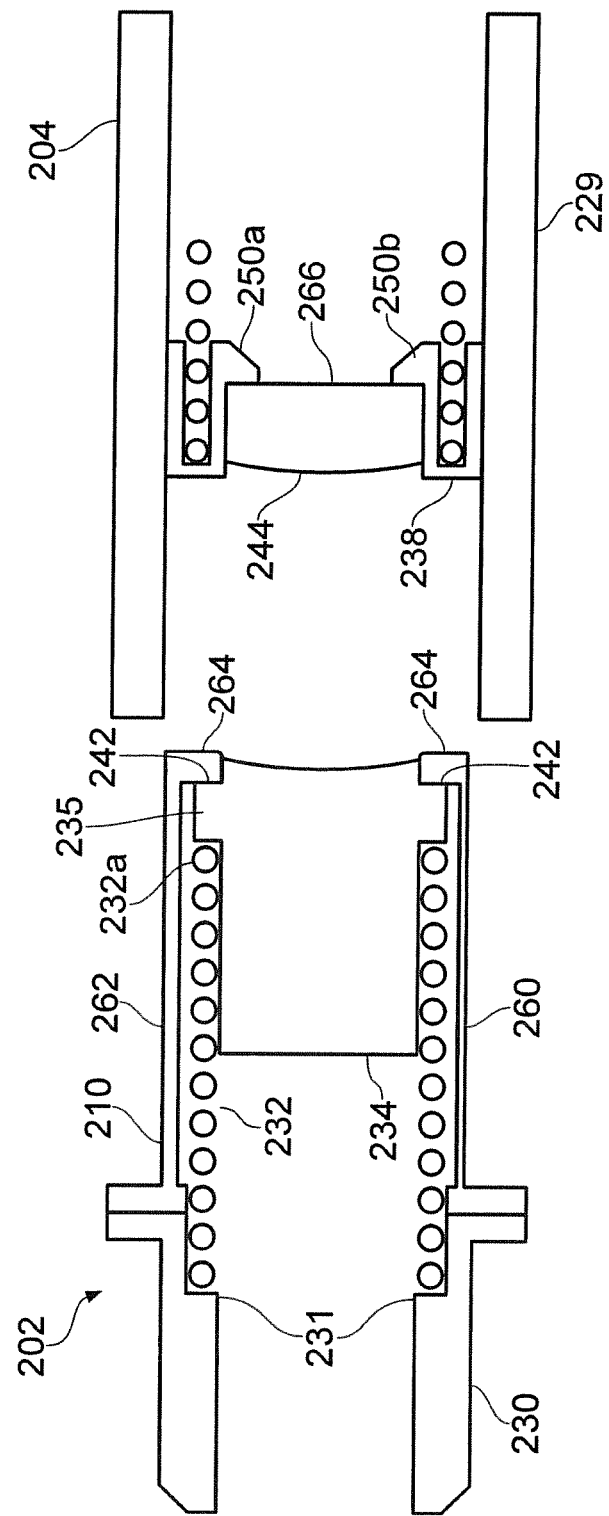
FIG. 13 is a cross-sectional view showing the male and female components of the apparatus of an aspect of the present invention disposed prior to engagement.

Turning now to FIG. 13, a schematic illustration of a cross-section of assembly 200 prior to coupling respective male and female components together shows further respective male and female components assembled and ready for coupling together. Male component 202 has the plunger guide 210 and end cap connected together and spring 232 is partially compressed such that one end, 232a, abuts shoulder 235 of plunger 234 and the other end abuts an interior formation 231 of the male component 202, in the illustrated case a formation on end cap 230. The compression of spring 232 causes the engagement surface 242 of plunger 234 to be biased against and abut partially inwardly extending portion 264 of the plunger guide 210 side wall. The outer side wall 262 of plunger guide 210 is configured to be in slideable engagement with the inner wall of cylinder 229 when inserted into the female component 202. Also shown is a thinner section 260 of the side wall 262 which forms the bottom of groove 209 illustrated in previous figures.

The female component 204 is assembled and the catch members 250a and 250b of collar 238 are urged into abutment against the rear wall 266 of stopper 241 by biasing action of spring 240 which is entrapped in a structure not visible in the illustrated cross-section. The cross-section view illustrated in FIG. 10 is also from a perspective which does not show the strut 257 extending from the end wall 255 (also not shown) and supporting the stopper 241.

Figure 14:
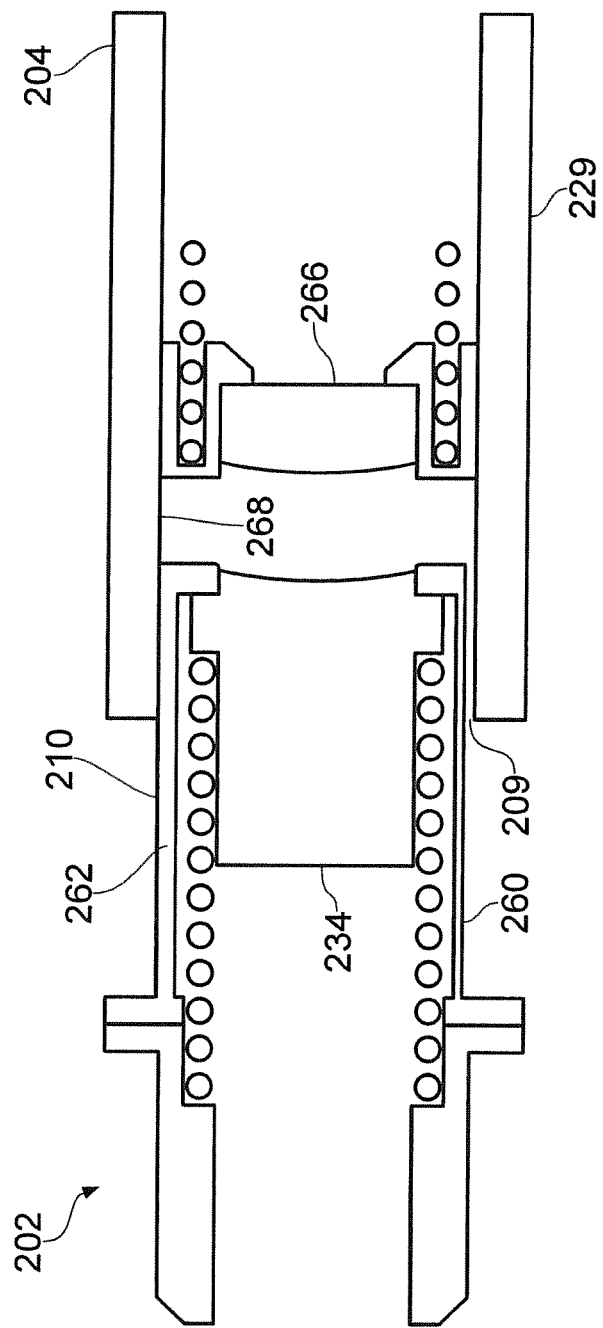
FIG. 14 is a cross-sectional view showing the male and female components of the apparatus of an aspect of the present invention disposed in an intermediate stage leading to secure and sealed engagement.

FIG. 14 is a schematic illustration of the male component 202 partially inserted into the female component 204. The slideable engagement of plunger guide 210 outer wall 262 with the inner wall 268 of cylinder 229 is clearly illustrated. Additionally, groove 209 can be seen to be in the process of being formed between the thinner portion 260 of the plunger guide wall and the corresponding part of the inner wall of cylinder 229.

Figure 15:
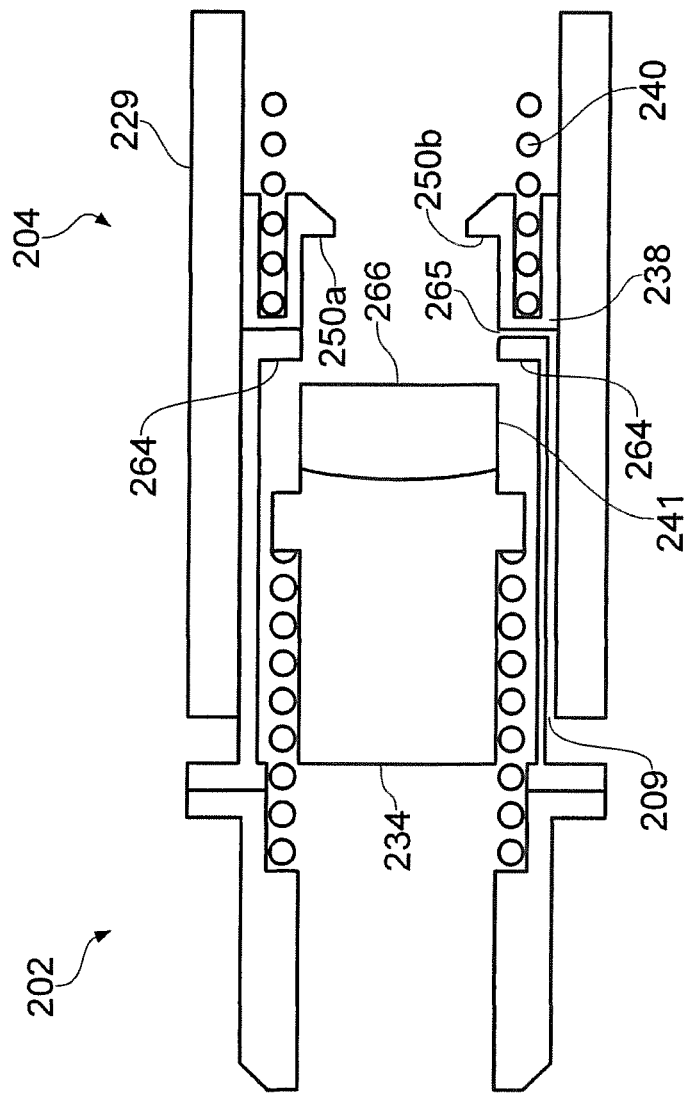
FIG. 15 is a cross-sectional view showing the male and female components of the apparatus of an aspect of the present invention disposed in secure and sealed engagement illustrating formation of a gas communication pathway and a liquid communication pathway.

FIG. 15 is a schematic illustration on the male component and female component fully engaged with each other. As can be seen, the travel of plunger guide into the cylinder 229 has caused the inwardly extending wall portion 264 to engage with collar 238 and force it back against spring 240. It should be noted that groove 209 extends along the inwardly extending wall 264 in the region 265 to form a gas pathway from groove 209 into the interior of cylinder 229. The gas pathway 265/209 provides a venting mechanism for air to escape from a reservoir being filled with a liquid but also may provide for the ingress of air into a bottle from which the liquid is being supplied to the reservoir.

Stopper 241 engages with plunger 234 to prevent it travelling with the plunger guide 210 and forces it back against spring 232 to open a gap between the male component 202 and the female component 204 thereby opening both the valve element of the male component 202 and the valve element of the female component 204 to provide a liquid pathway between the male and female components.

Figure 16:
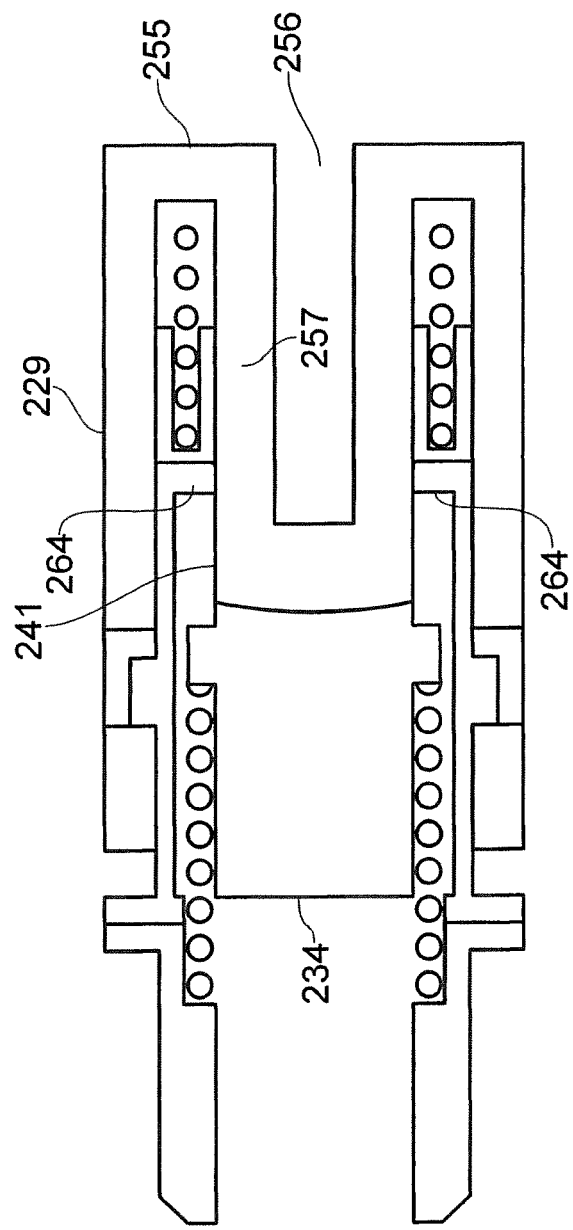
FIG. 16 is a cross-sectional view showing the male and female components of the apparatus of an aspect of the present invention disposed in secure and sealed engagement from a different perspective.

Turning now to FIG. 16, a cross-section is illustrated from a different perspective to that illustrated in FIG. 15 which illustrates the structure and arrangement of cylinder 229 and how stopper 241 is supported. As can be seen from FIG. 16, end wall 255 extends inwardly to form strut 257. Strut 257 is not of continuous tubular form but is discontinuous to allow a liquid to pass around stopper 241 into cavity 256.

Groove 209/265 cannot be seen in FIG. 16 as the groove is narrow and not visible from the perspective from which the cross-section shown in FIG. 16 is viewed.

Figure 17:
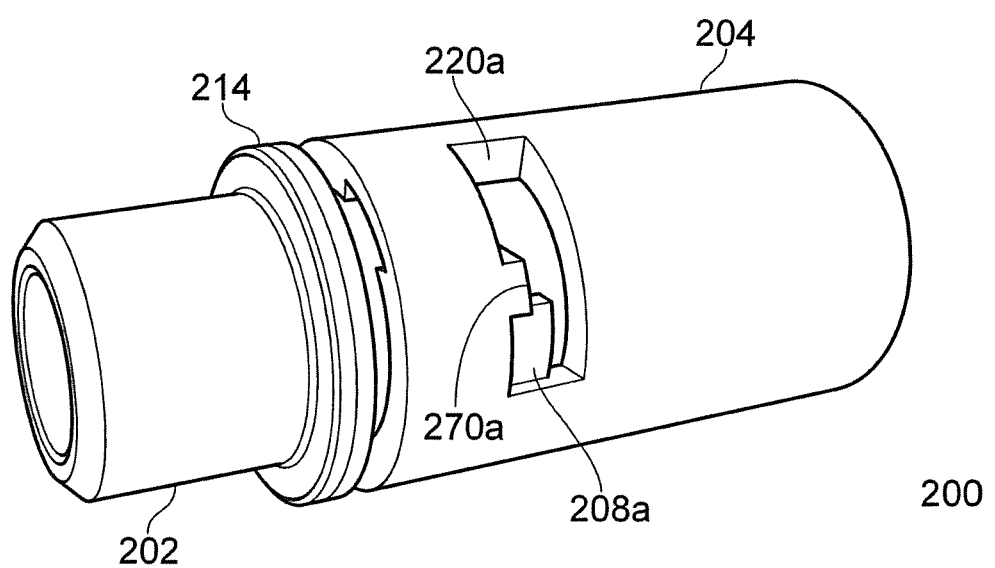
FIG. 17 is a perspective view showing the male and female components of the apparatus of an aspect of the present invention disposed in an intermediate stage prior to secure and sealed engagement.

FIG. 17 illustrates the locking/coupling arrangement between the male component 202 and female component 204 with reference to slot 220a in an intermediate stage just prior to full locking. As can be seen, slot 220a includes a barrier portion 270a. When plunger guide 210 is inserted into cylinder 229 tongue 208a travels through guide 206a to slot 220a. The material of cylinder 229 and/or tongues 208 and/or plunger guide 210 may be resiliently deformable, for example the material may be a suitable plastics material. Optionally, the tongues 208 may be movably biased away from the outer wall of the plunger guide.

Figure 18:
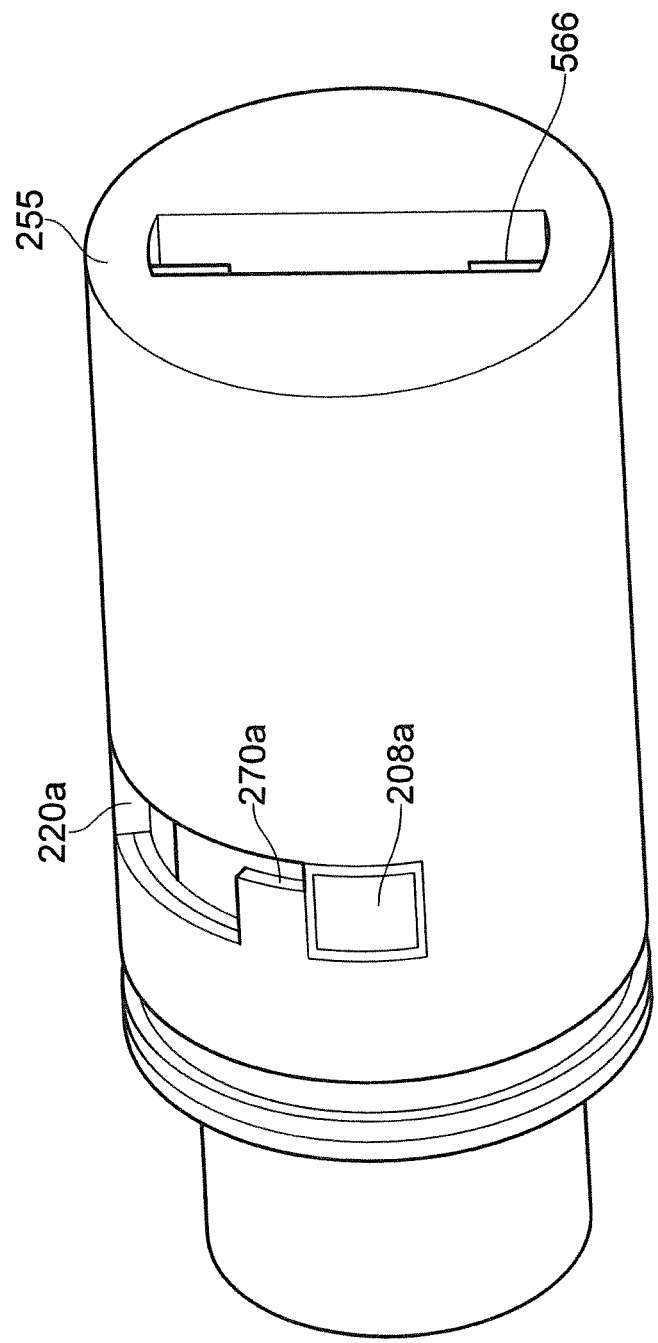
FIG. 18 is a perspective view showing the male and female components of the apparatus of an aspect of the present invention disposed in a secure and sealed engagement.

When tongue 208a reached slot 220a it engages with the slot and twisting of plunger guide 210/male component 202 and pressure against spring 240 will cause tongue 208a to pass around barrier 270a. Releasing pressure against spring 240 will cause plunger guide 210 to be forced back and behind barrier 270a thereby locking the male component 202 to the female component 204 through the action of the bias of spring 240. Such action may provide a "snap-fit" type of engagement. This makes it relatively difficult to separate the male and female components from each other and inhibits minor separation which would cause leakage of liquid from the assembly without closing respective valve elements of the male and female components. FIG. 18 illustrates the locking mechanism when the tongue 208a is fully engaged with slot 220a in the locked position.

Figure 19:
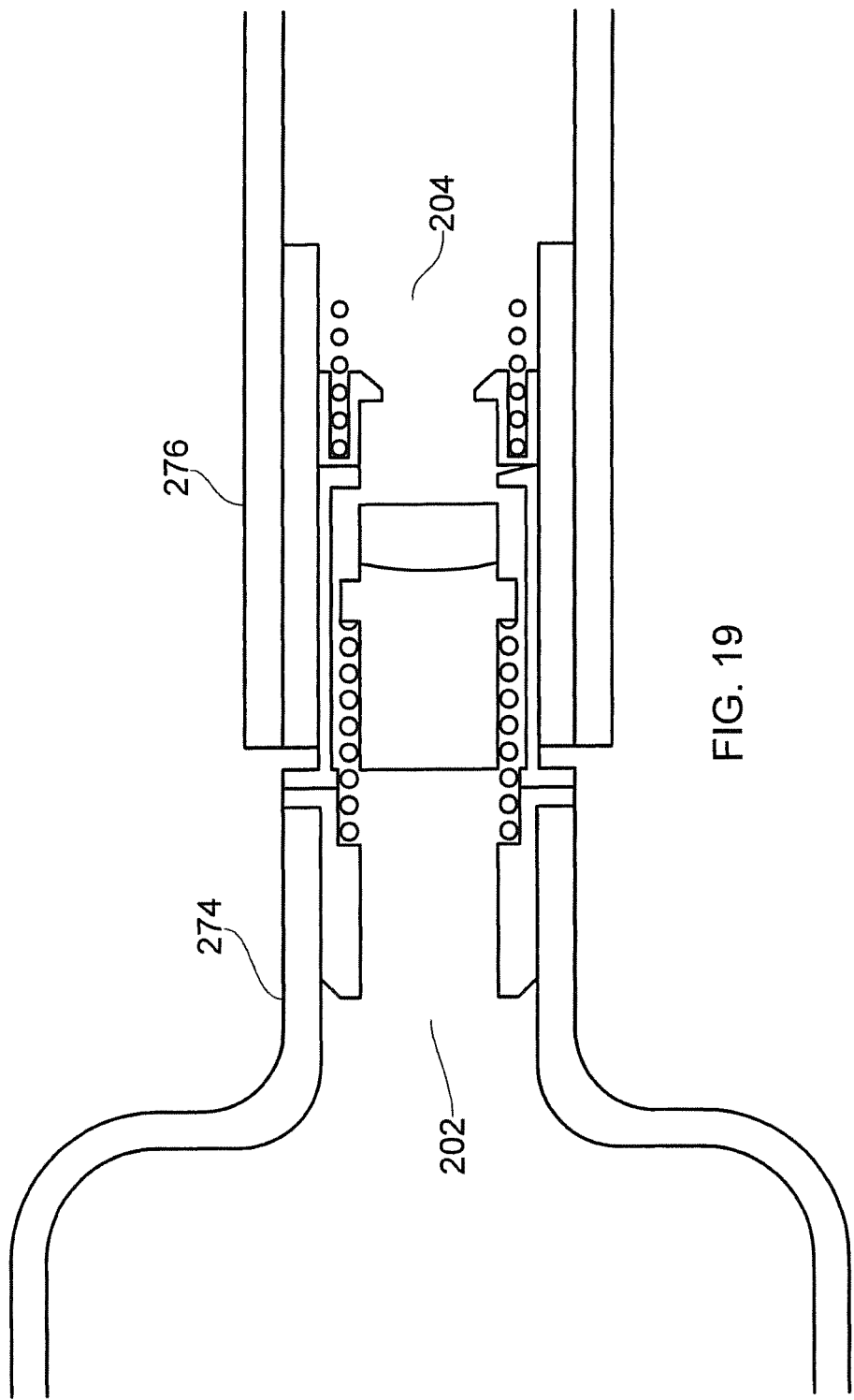
FIG. 19 is a cross-sectional view showing a portion of a dispenser disposed in secure and sealable engagement with a smoking-substitute device.
Figure 20:
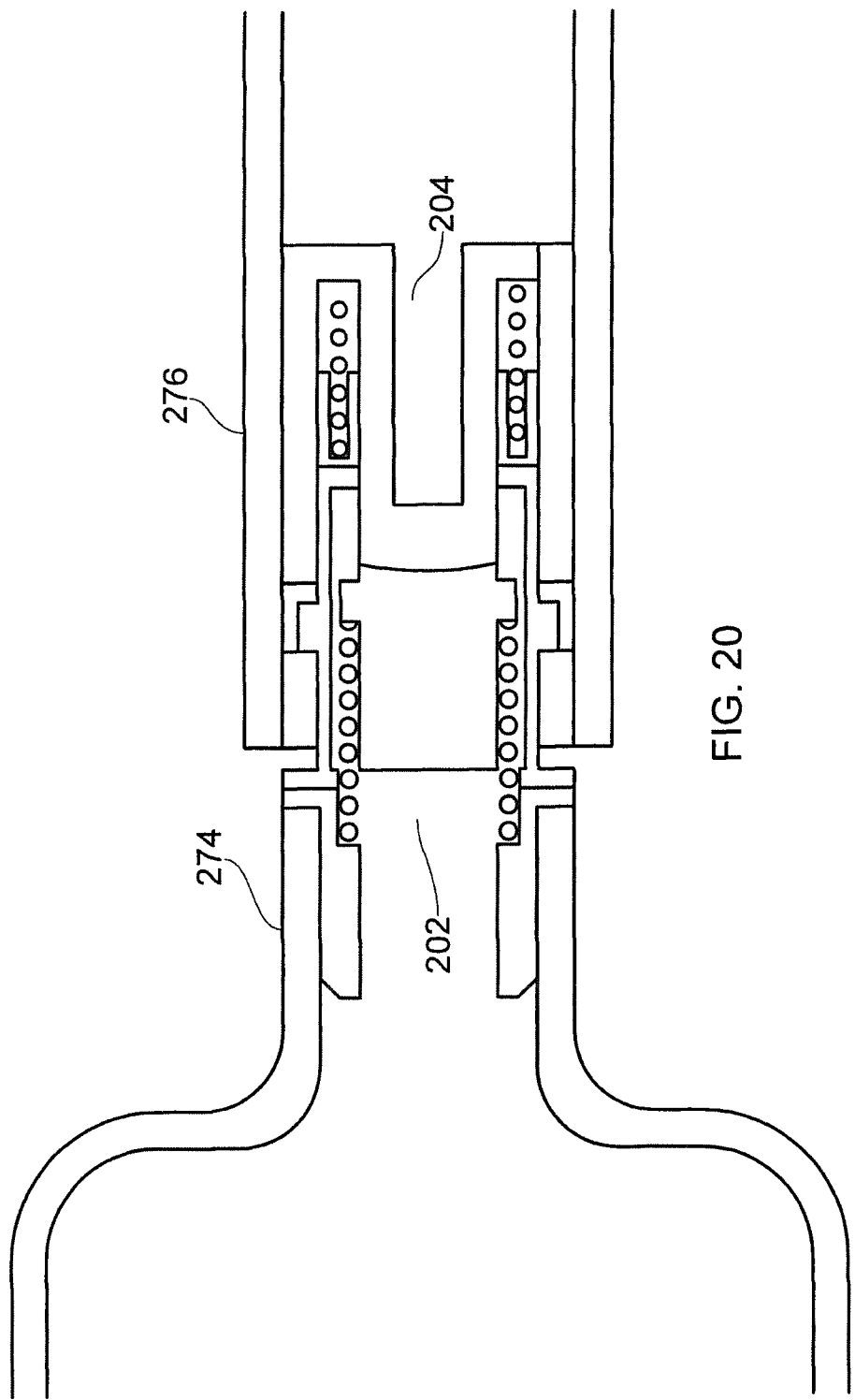
FIG. 20 is a cross-sectional view showing the portion of the dispenser disposed in secure and sealable engagement with the smoking-substitute device from a different perspective.

Turning now to FIG. 19, use of the assembly for dispensing liquid from a bottle into the reservoir of an electronic smoking device is illustrated in cross-section. The male component 202 of the assembly is disposed in the neck of a liquid dispenser bottle 274. The female component 204 of the assembly is disposed in the reservoir of a smoking-substitute device, e.g. e-cigarette, 276. Respective male and female components 202 and 204 are respectively fitted to the neck of dispenser bottle 274 and inlet to the reservoir of the smoking device 276. Before insertion respective valve elements of male and female components 202 and 204 are closed. When the components are inserted one within the other to form the assembly they are locked together and respective valve elements opened to permit liquid to flow from dispenser bottle 274 to the reservoir of smoking-substitute device 276. FIG. 20 is an illustration of the arrangement of FIG. 19 but from a different perspective that shows the strut supporting the stopper 241.

The slideable fit between the male and female components 202 and 204 is configured to inhibit flow of liquid and so should be too narrow to encourage a capillary action to draw a liquid between the interface of the outer wall 262 of the male component 202 and the inner wall of the cylinder 229 of the female component 204. In that regard it is not a so-called interference fit but a transitional fit permitting close slideable engagement yet inhibits the flow of liquid.

Figure 21:
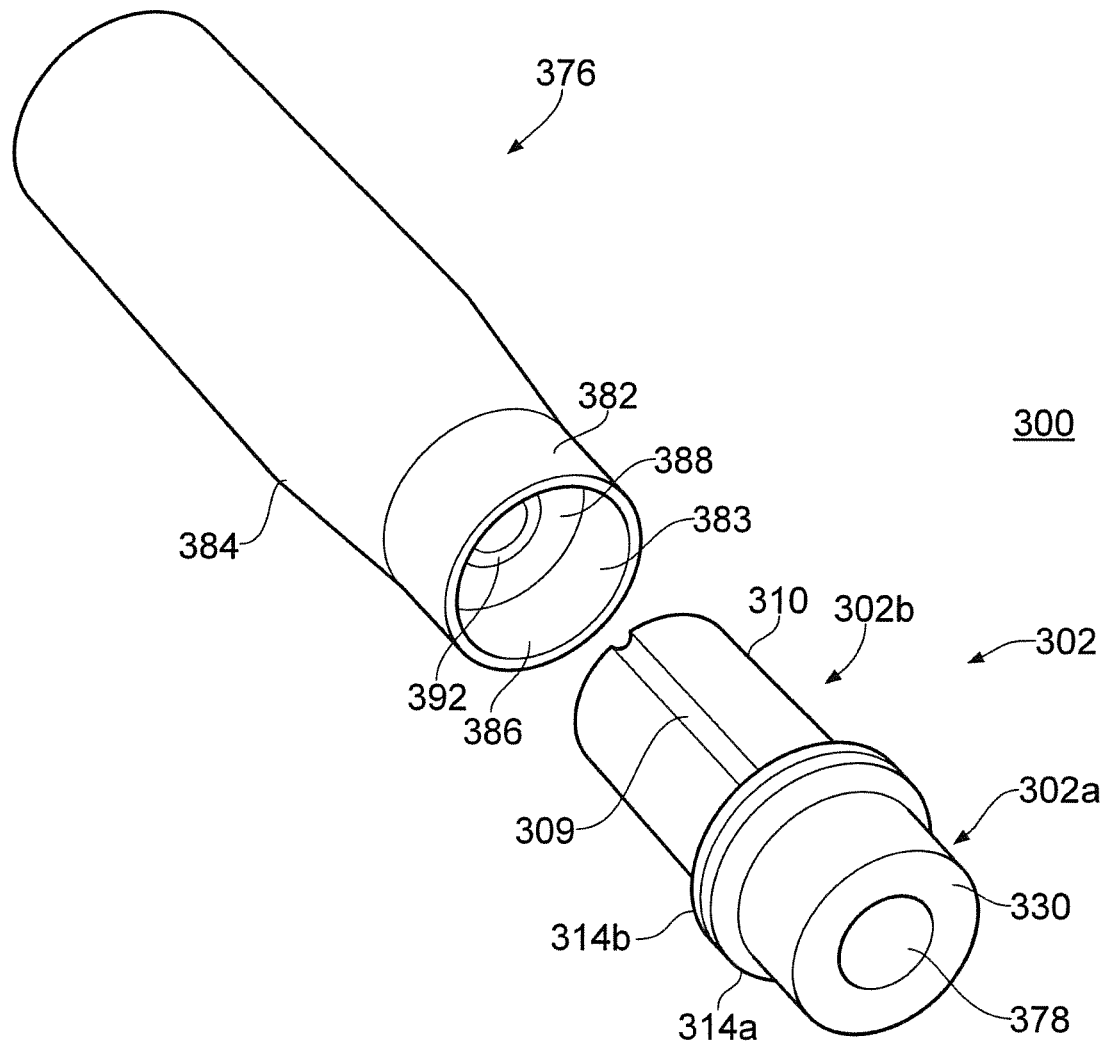
FIG. 21 is an exploded perspective view illustration showing an apparatus according to another aspect of the present invention and a cartomizer portion of a smoking-substitute device configured to receive the apparatus in an uncoupled configuration.
Figure 22:
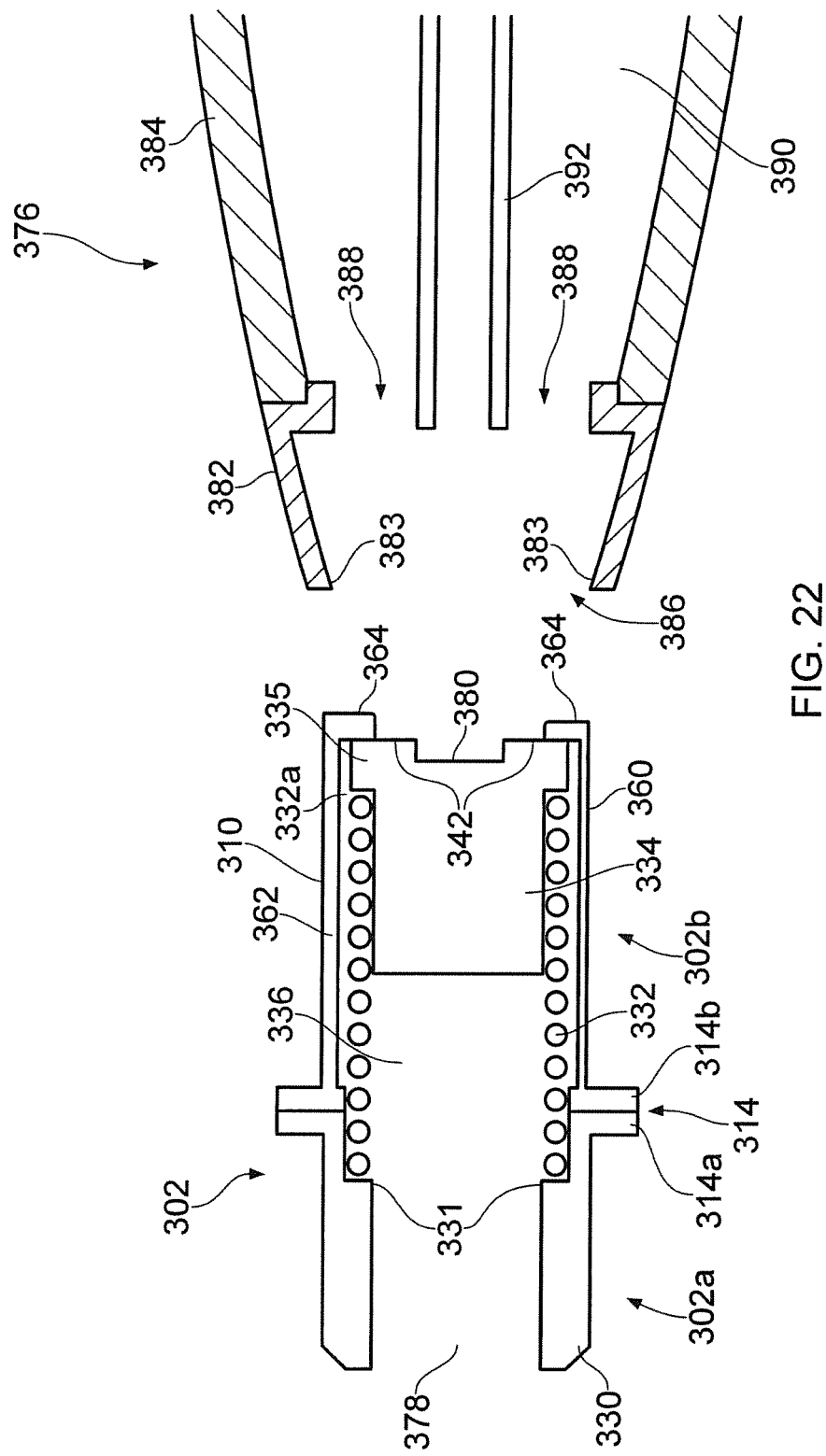
FIG. 22 is a cross-sectional view of the apparatus and a cartomizer portion of a smoking-substitute device illustrated in FIG. 21 in the uncoupled configuration.

FIGS. 21 and 22 illustrate an apparatus according to another aspect of the present invention and a cartomizer portion of a smoking-substitute device configured to receive the apparatus FIGS. 21 and 22 (and further FIGS. 23 to 34) are described with reference to a cartomizer portion of smoking-substitute device. The cartomizer portion may be removable and/or replaceable from a body portion of a smoking-substitute device, or may be integrally formed with the body portion of the smoking-substitute device.

Features similar to those illustrated in FIGS. 6 to 8, 10 and 13 to 15 are also illustrated in FIGS. 21 and 22. In FIGS. 21 and 22, the features common with those of FIGS. 6 to 8, 10 and 13 to 15 are designated with reference numerals of the type 3XX rather than 2XX. Thus, in FIGS. 21 and 22, the apparatus is denoted by reference number 300 (rather than 200) and so on.

FIG. 21 is a perspective view of an apparatus 300 and a cartomizer portion 376 of a smoking-substitute device in an uncoupled configuration and FIG. 22 illustrates the same elements from a different perspective (i.e. a cut-away side view). The apparatus 300 comprises an assembly 302 which is similar to the male component 202 described previously.

Cartomizer 376 is shown in FIGS. 21 and 22 with a mouthpiece section removed. The illustrated features of the cartomizer 376 comprise a mouthpiece port 382 and a body section 384. Mouthpiece port 382 comprises a hollow section open at both ends and configured to receive an end of a mouthpiece (not shown) in an aperture 386 at a first end thereof. An aperture 388 at a second end of mouthpiece port 382 provides fluid communication between the mouthpiece port 382 and both a liquid reservoir 390 and a gas passageway 392 of the body section 384. When a mouthpiece end is located within the mouthpiece port 382, aperture 388 is partly sealed by the end of the mouthpiece to provide fluid communication with gas passageway 392 only. This is to prevent liquid contained in liquid reservoir 390 from leaking from the reservoir 390.

During a re-filling process, the mouthpiece is removed from the mouthpiece port 382, leaving the cartomizer 376 in the state as illustrated.

With the cartomizer 376 in this state, the assembly can be slid into the mouthpiece port 382 to undertake the re-filling process.

Exterior wall 362 (not shown in FIG. 21) of plunger guide 310 of the assembly 302 is slideably engageable with an interior wall 386 of the mouthpiece port 382 other than in the region of wall 362 comprising groove 309.

The assembly 302 comprises a flange 314 formed to provide a convenient abutment of two parts, 302a and 302b, of the assembly 302 which are manufactured as separate units to allow for assembly of the other elements of the assembly 302 as will be evident from the later description.

Referring now to FIG. 22, which shows the assembly 302 prior to location within the mouthpiece port 382 of the cartomizer portion 376 of a smoking-substitute device, the two part configuration of assembly 302 is clearly illustrated and comprises plunger guide 310 and an end cap 330. The plunger guide 310 has a flange 314b and end cap 330 has a flange 314a which facilitates joining respective parts, plunger guide 310 and end cap 330, together. A helical coil spring 332 is inserted into the end cap 330 and a plunger 334 extends through the middle of helical coil spring 332 so that a shoulder 335 on the plunger 334 may contact end 332a of the spring 332. The plunger 334 is inserted into the hollow cylindrical cavity 336 of plunger guide 310 of the assembly 310. The respective parts of assembly 302 may then be assembled.

As can be seen, shoulder 335 includes an engagement surface 342 and a sealing surface 380.

End cap 330 is formed with an aperture 378 at an end thereof remote from the flange 314a.

As can be seen in FIG. 22, the plunger guide 310 and end cap 330 are connected together and spring 332 is partially compressed such that one end, 332a, abuts shoulder 335 of plunger 334 and the other end abuts an interior formation 331 of the assembly 302 (in the illustrated case a formation on end cap 330). The compression of spring 332 causes the engagement surface 342 of plunger 334 to be biased against and abut partially inwardly extending portion 364 of the plunger guide 310 side wall. The outer side wall 362 of plunger guide 310 is configured to be in slideable engagement with a portion 383 of the inner wall of mouthpiece port 382 when inserted into cartomizer 376. Also shown is a thinner section 360 of the side wall 362 which forms the bottom of groove 309 illustrated in FIG. 21.

Figure 23:
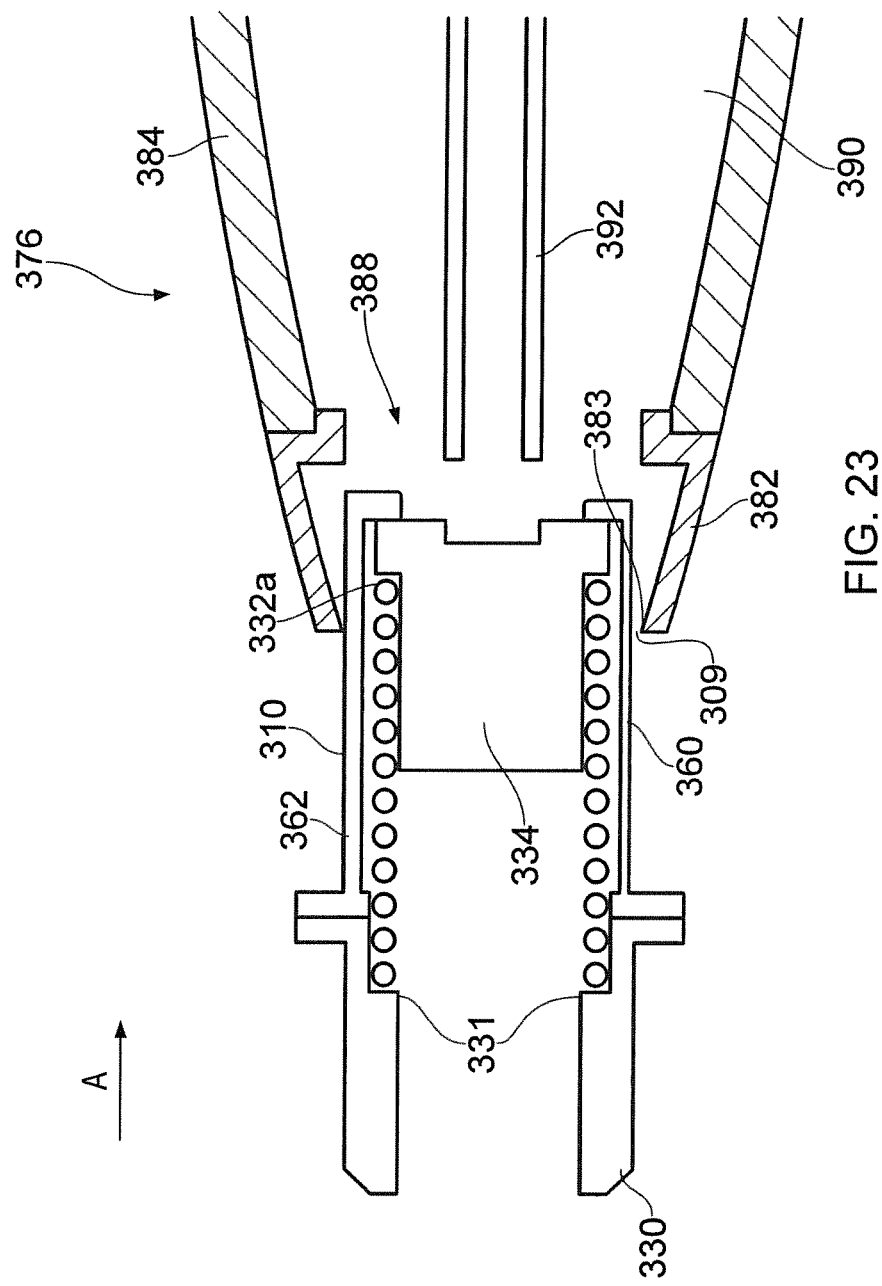
FIG. 23 is a cross-sectional view showing the apparatus according to another aspect of the present invention and a cartomizer portion of a smoking-substitute device configured to receive the apparatus disposed in an intermediate stage between the uncoupled configuration and a coupled configuration.

FIG. 23 is a schematic illustration of the assembly 302 partially inserted into the cartomizer 376. Not all reference numerals are shown in this figure for clarity purposes. The slideable engagement of plunger guide 310 outer wall 362 with the portion 383 of the inner wall of mouthpiece port 382 is clearly illustrated. Additionally, groove 309 can be seen to be in the process of being formed between the thinner portion 360 of the plunger guide wall and the corresponding portion 383 of the inner wall of mouthpiece port 382. Advancing the assembly 302 toward the cartomizer 376 in a direction indicated by arrow A will bring the assembly 302 and the cartomizer 376 closer to full engagement.

Figure 24:
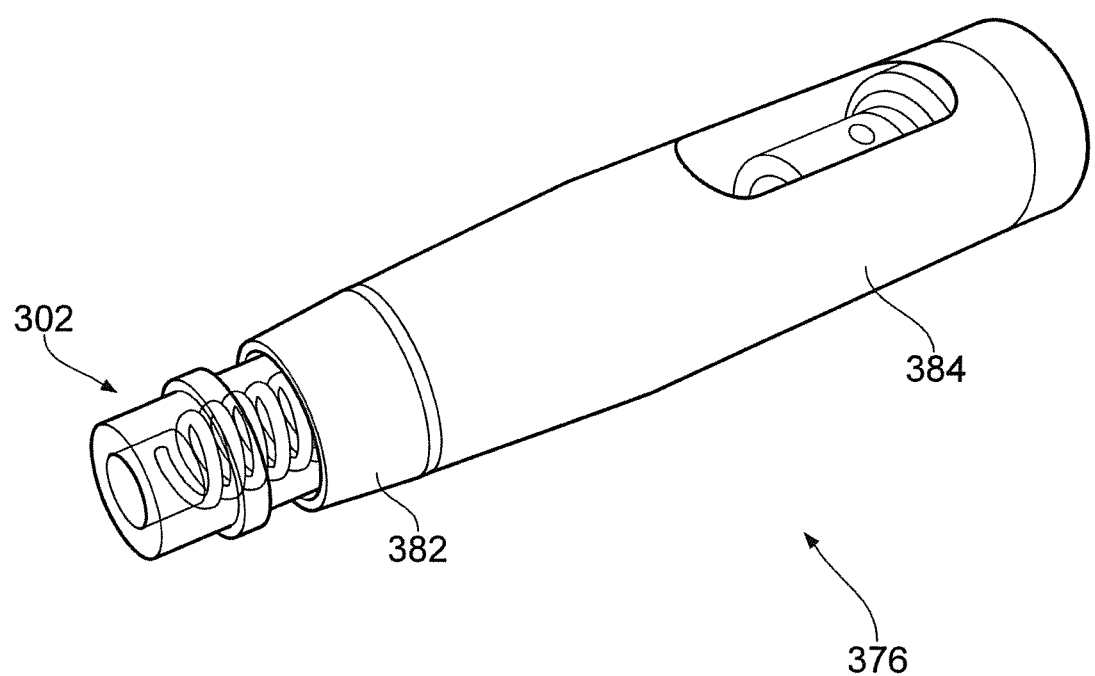
FIG. 24 is a perspective view illustrating the apparatus according to the another aspect of the present invention and a cartomizer portion of a smoking-substitute device in a coupled configuration.
Figure 25:
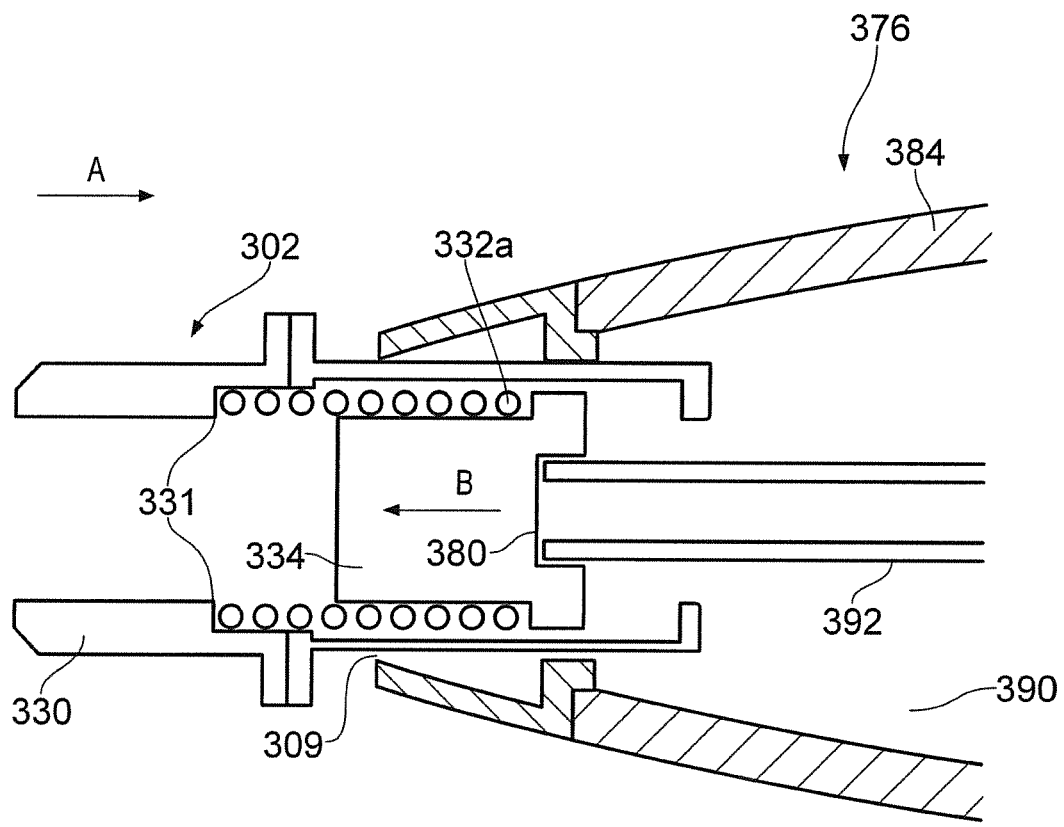
FIG. 25 is a cross-sectional view of the apparatus and a cartomizer portion of a smoking-substitute device illustrated in FIG. 21 in the coupled configuration.

FIG. 24 is an illustration of the assembly 302 and cartomizer 376 fully engaged with each other and FIG. 25 is a schematic illustration showing a cross-sectional side view of the assembly 302 and cartomizer 376 fully engaged with each other. As can be seen, the travel of plunger guide 310 into the mouthpiece port 382 in the direction indicated by arrow A has caused sealing surface 380 of plunger to abut an end of a tube forming the gas passageway 392 and force it (and thus plunger 334) back against spring 332. It should be noted that groove 309 extends along wall 360 to form a gas pathway from groove 309 into the liquid reservoir 390 of body section 384. The gas pathway provides a venting mechanism for air to escape from a reservoir being filled with a liquid but also may provide for the ingress of air into a bottle from which the liquid is being supplied to the reservoir.

Forcing the plunger 334 back in this manner (i.e. in the direction indicated by arrow B) causes a gap to open between the shoulder 335 of plunger 334 and the inwardly extending portion 364 of the plunger guide 310 side wall thereby opening a valve element of the assembly 302 to provide a liquid pathway through the assembly 302.

Typically, a re-filling process will be conducted with the assembly 302 and cartomizer 376 substantially vertical with the assembly 302 above the cartomizer 376. When held in this manner, liquid to be dispensed will travel in the direction of arrow A under the influence of gravity down through the assembly 302 and into the cartomizer 376.

Figure 26:
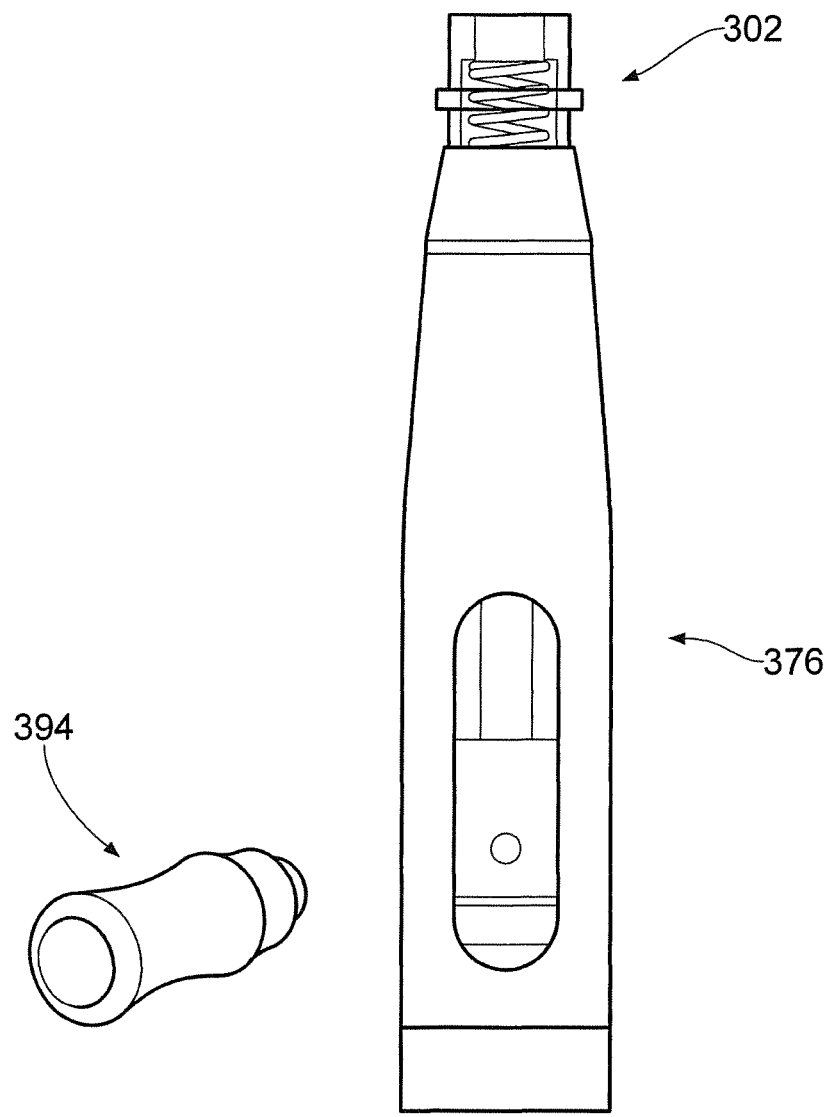
FIG. 26 is a side view illustrating the features illustrated in FIG. 24 from a different perspective.

FIG. 26 is an illustration of the assembly 302 and cartomizer 376 fully engaged with each other, with a removed mouthpiece 394 also shown.

Figure 27:
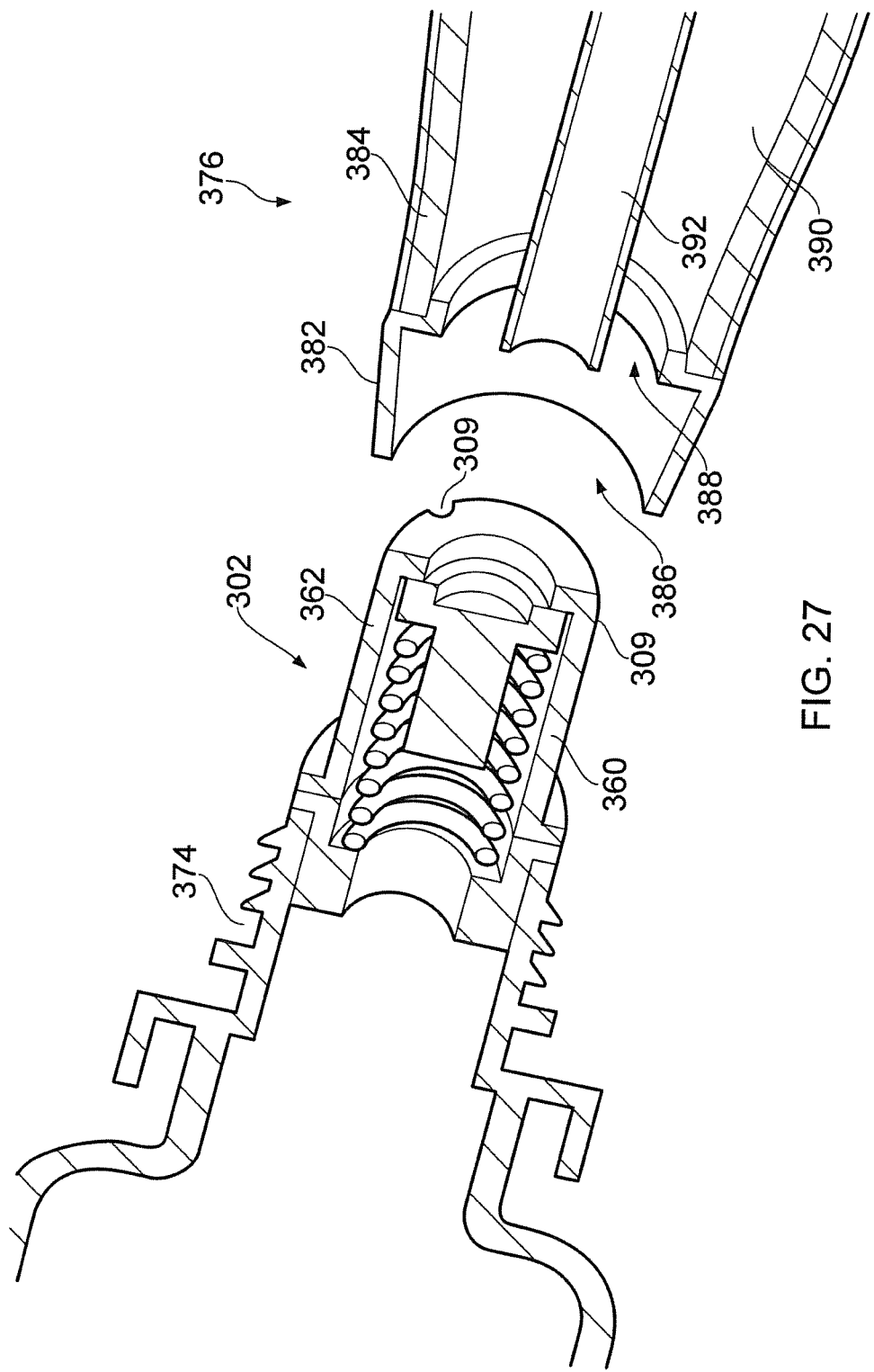
FIG. 27 is a cross-sectional view illustrating the apparatus of another aspect of the present invention and a cartomizer portion of a smoking-substitute device in the uncoupled configuration and a dispenser bottle coupled to the apparatus.
Figure 28:
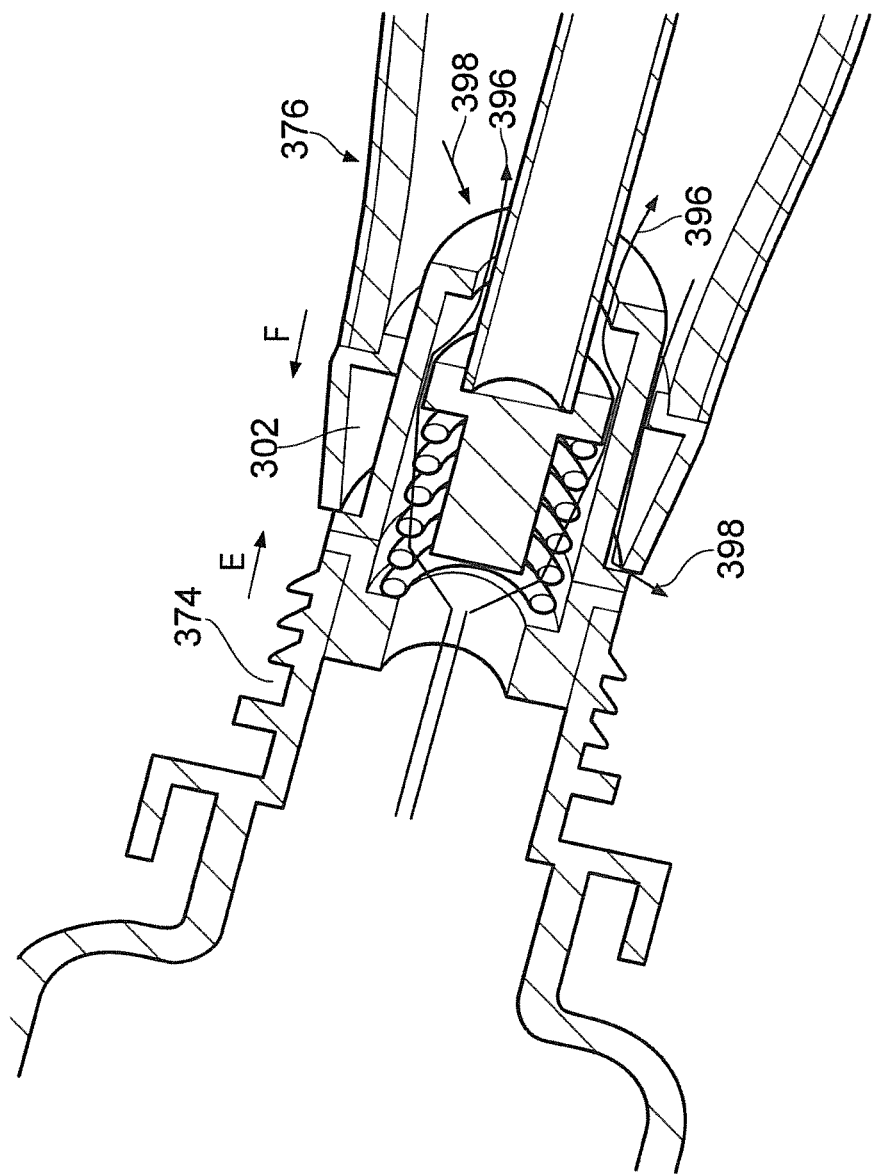
FIG. 28 is a cross-sectional view illustrating the apparatus according to another aspect of the present invention and a cartomizer portion of a smoking-substitute device in the coupled configuration and the dispenser bottle coupled to the apparatus.

Turning now to FIGS. 27 and 28, use of the assembly 302 for dispensing liquid from a bottle into the liquid reservoir 390 of the cartomizer 376 is illustrated in perspective cross-section in both figures. FIG. 27 shows the assembly 302 and cartomizer 376 in the uncoupled configuration and FIG. 28 shows the assembly 302 and cartomizer 376 in the coupled configuration. The assembly 302 is disposed in the neck of a liquid dispenser bottle 374. Before insertion of the assembly 302 into the mouthpiece port 382 of the cartomizer 376 (i.e. as shown in FIG. 27) the valve elements of assembly 302 is closed. With the assembly 302 inserted in the mouthpiece port 382 of the cartomizer 376 (i.e. as shown in FIG. 28), and upon application of a force denoted by arrow E to dispenser bottle 374 and an oppositely directed force denoted by arrow F to the cartomizer 376, the valve element is opened to permit liquid to flow from dispenser bottle 374 to the liquid reservoir 390 of cartomizer 376. Liquid flow from the dispenser bottle 374 to the liquid reservoir 390 of cartomizer 376 is illustrated in FIG. 28 by way of arrows 396.

Gas displaced from the liquid reservoir 390 as a result of the liquid being added is vented from the liquid reservoir 390 via a gas pathway formed by groove 309. Gas flow from the liquid reservoir 390 of cartomizer 376 is illustrated in FIG. 28 by way of arrows 398.

The displaced gas may, for example, be vented to atmosphere (as shown in FIG. 28). Optionally, the groove 309 may be configured to form a gas pathway for venting the displaced gas into the dispenser bottle 374.

Figure 29:
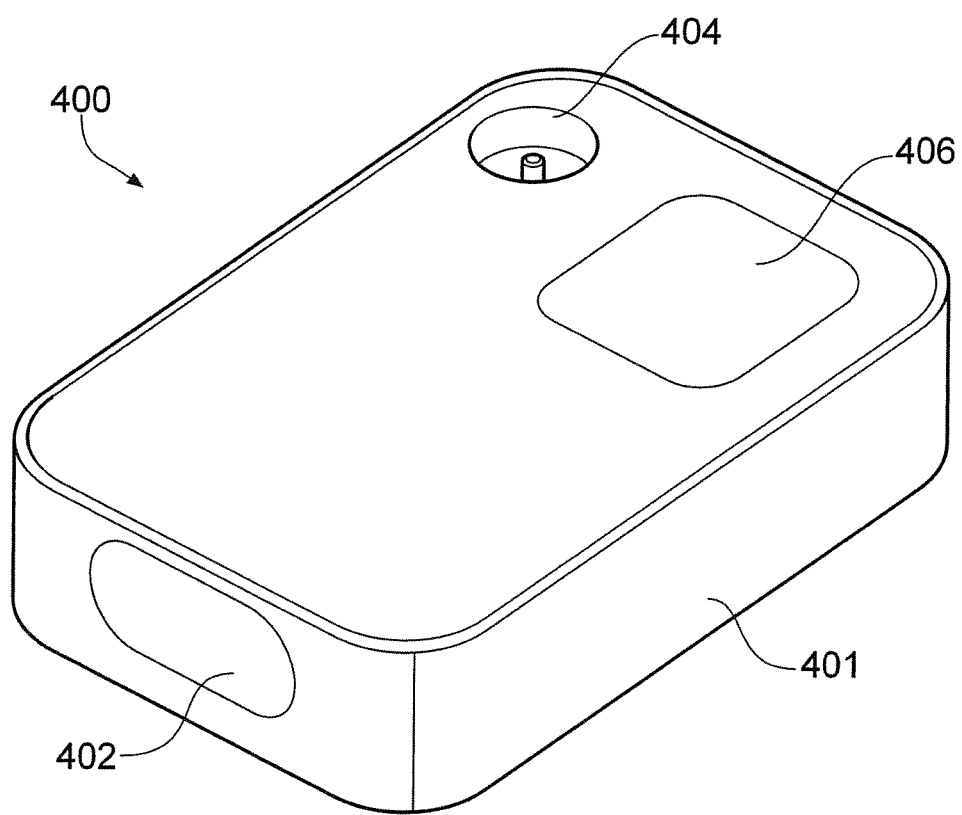
FIG. 29 is a perspective view illustrating a filling station apparatus according to yet another aspect of the present invention.

FIG. 29 shows a perspective view of a filling station apparatus 400. The filling station apparatus 400 comprises a housing 401 in which are formed a dispenser bottle receiving port 402 and a device receiving port 404. An activation button 406 is also provided on the housing 401 for controlling operation of the filling station apparatus 400.

Dispenser bottle receiving port 402 is configured to receive a dispensing end of a dispenser bottle. A device receiving port 404 is configured to receive a filling end of a cartomizer of a smoking-substitute device. The dispenser bottle receiving port 402 is in fluid communication with the device receiving port 404 via a fluid conduit (not shown) located within the housing.

The filling station apparatus 400 further comprises a pumping arrangement (not shown) the operation of which is controlled by the activation button 406. In operation, the pumping arrangement serves to exert a pressure on a dispenser bottle located within the dispenser bottle receiving port 402 to expel liquid from the dispenser bottle to the fluid conduit. The pumping arrangement is also operative to cause dispensed liquid to flow through the fluid conduit to the device receiving port 404 at which point it flows into a cartomizer portion of a smoking-substitute device located in the device receiving port 404.

The filling station apparatus 400 may be suitable for implementing an automatic refilling operation of a cartomizer or smoking-substitute device. The configuration of the filling station apparatus 400 is such that it may be suitable for location on a flat surface such as, for example, a table, or desk.

The device receiving port 404 may comprise a smoking-substitute device engaging portion (e.g. 204 or 302b) of a coupling assembly 200 or 300, such as those described above (e.g. a coupling assembly as described in relation to FIGS. 6 to 20, or a coupling assembly as described in relation to FIGS. 21 to 28). The other end of such coupling assemblies 200, 300, where present, may connect with an end of the fluid conduit within the housing.

In an optional arrangement, the device receiving port 404 may comprise a cartomizer or smoking-substitute device engaging portion of any other suitable type.

The pumping arrangement may be powered by an electrical power source. In such an arrangement, the activation button 406 may simply be an on/off switch. In an optional arrangement, the pumping arrangement may be mechanically powered via user operation of said the activation button 406. In this optional arrangement, pumping may be achieved by a user pressing the activation button 406 repeatedly. In a yet further optional arrangement, the apparatus 400 may comprise a pumping arrangement which comprises a combination of the above-described electrically and mechanically powered arrangements.

Figure 30:
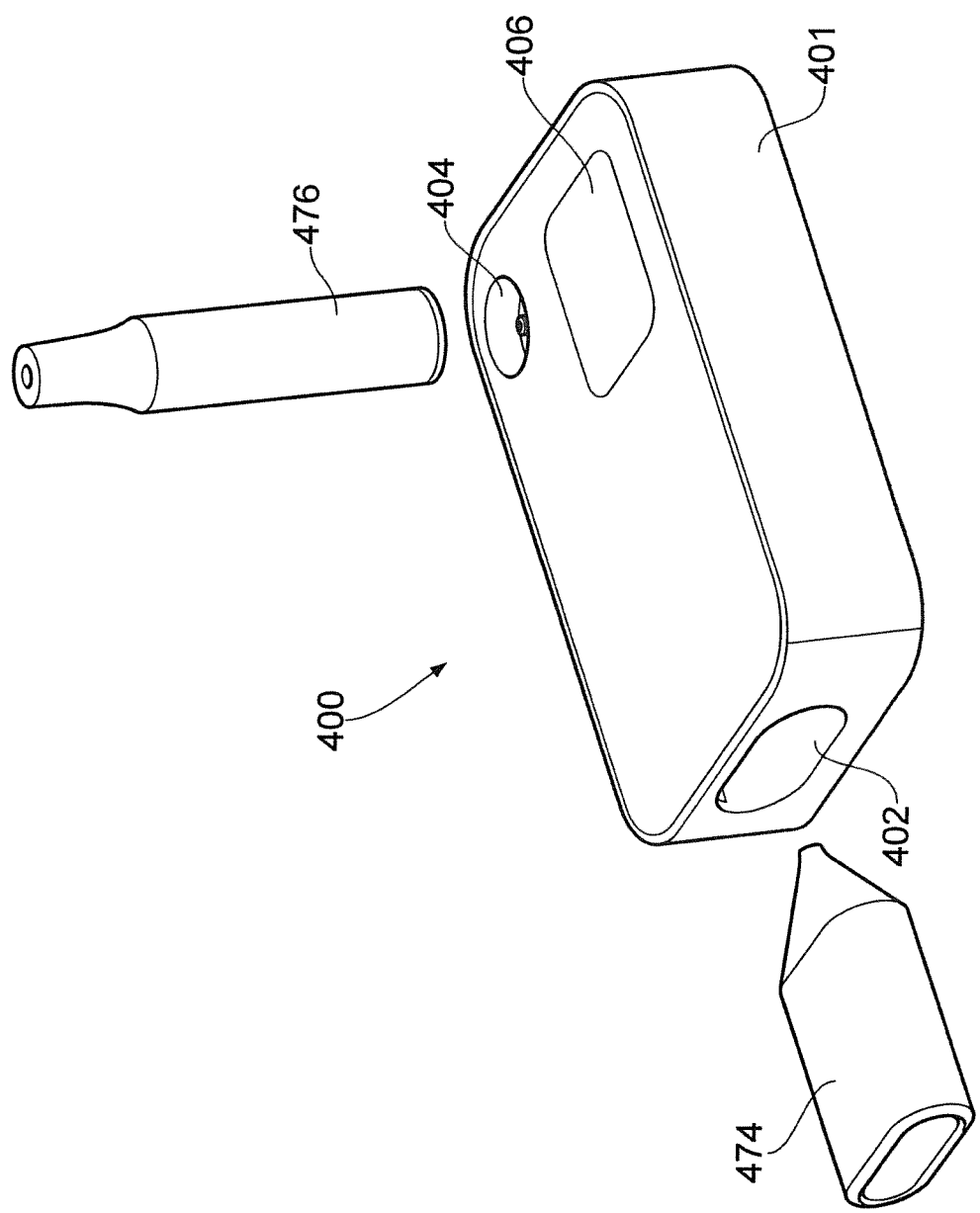
FIG. 30 is a perspective view illustrating the filling station according to the yet another aspect of the present invention, a dispenser and a cartomizer portion of a smoking-substitute device in an uncoupled configuration.

FIG. 30 shows the filling station apparatus 400 of FIG. 29, and also a liquid dispenser bottle 474 and a cartomizer 476 of a smoking-substitute device. The liquid dispenser bottle 474 and cartomizer 476 of the smoking-substitute device are shown in an uncoupled configuration (i.e. they are shown disposed prior to coupling) with their respective receiving ports 402, 404.

Figure 31:
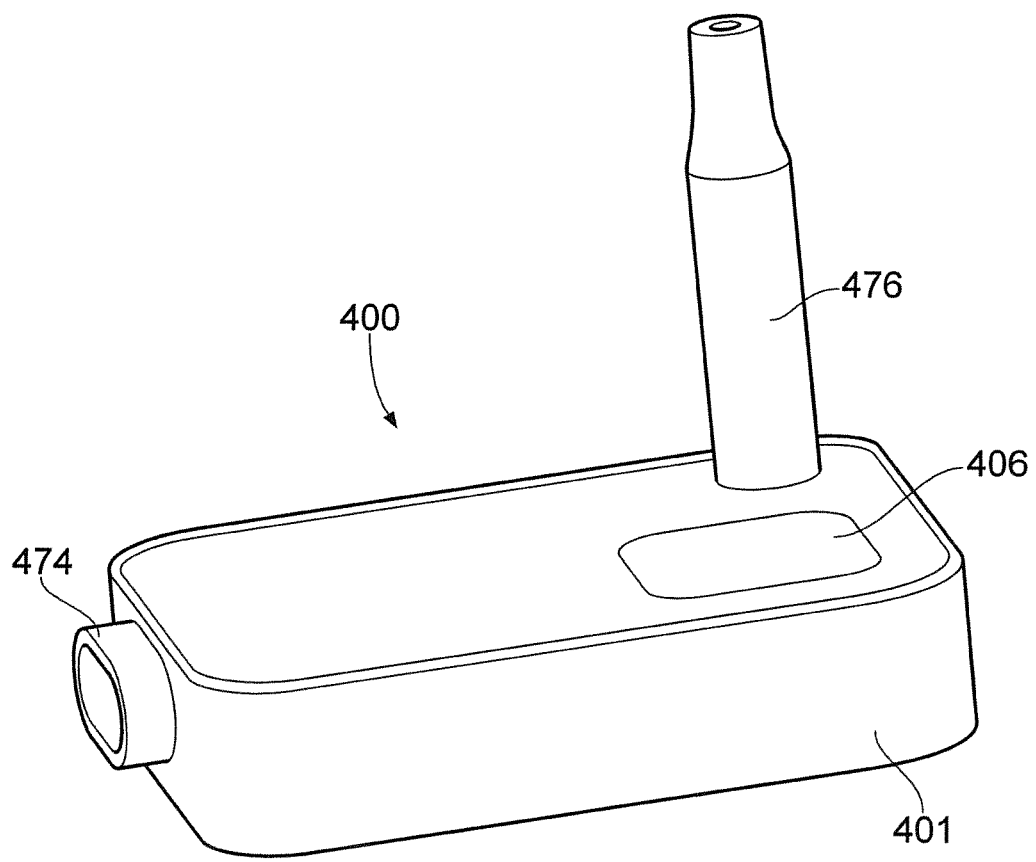
FIG. 31 is a perspective view illustrating the filling station according to the yet another aspect of the present invention, the dispenser and a cartomizer portion of a smoking-substitute device in a coupled configuration.

FIG. 31 shows the filling station apparatus 400 of FIG. 29, and also the liquid dispenser bottle 474 and the cartomizer 476 of the smoking-substitute device 476 in their respective coupled configurations.

The dispenser bottle receiving port 402 is configured to securably and sealably engage the liquid dispenser bottle 474. Such engagement may inhibit spillage of liquid from the bottle 474 or the filling station apparatus 400 when bottle 474 is coupled to the filling station apparatus 400.

The device receiving port 404 is configured to sealably cooperate with the cartomizer 476 of the smoking-substitute device. Such an arrangement may inhibit spillage of liquid from the cartomizer 476 of the smoking-substitute device or the filling station apparatus 400 when cartomizer 476 of the smoking-substitute device is coupled to the filling station apparatus 400.

Optionally, device receiving port 404 may be further configured for securably engaging said reservoir.

The apparatus described above in relation to FIGS. 29 to 31 may be suitable for filling cartomizers of smoking-substitute devices, or smoking-substitute devices themselves, of both a bottom-filling and a top-filling type. It may be particularly suitable for filling cartomizers or smoking-substitute devices of the bottom-filling type.

In an optional arrangement, the apparatus 400 of FIGS. 29 to 31 may be modified to be particularly suitable for filling cartomizers or smoking-substitute devices of the top-filling type. Such an arrangement is illustrated in FIG. 32.

Figure 32:
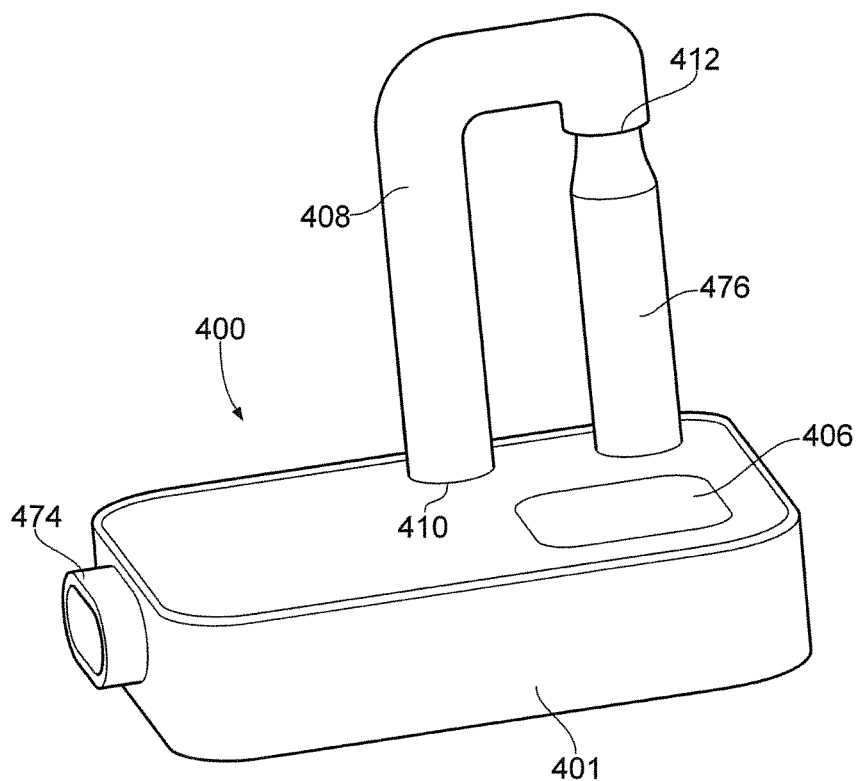
FIG. 32 is a perspective view illustrating an optional arrangement of the filling station.

In FIG. 32, the apparatus 400 further comprises a dispensing conduit 408. The dispensing conduit 408 is coupled to the apparatus 400 at one end 410 thereof. A remote end 412 of the dispensing conduit 408 is configured to receive a mouthpiece end of the cartomizer 476 of the smoking-substitute device.

In the illustrated arrangement, the device receiving port 404 simply comprises a seat for receiving a non-mouthpiece end of the cartomizer 476 of the smoking-substitute device. A port (not shown) for dispensing liquid to the cartomizer 476 of the smoking-substitute device is, in this arrangement, located at the remote end 412 of the dispensing conduit 408.

The end 410 of the dispensing conduit 408 is in fluid communication with the fluid conduit (not shown) located within the housing 401. In operation, therefore, liquid to be dispensed from the liquid dispenser bottle 474 to the cartomizer 476 of the smoking-substitute device passes from the liquid dispenser bottle 474 into the fluid conduit (via the dispenser bottle receiving port 402), through the dispensing conduit 408, through the port in the remote end 412 of the dispensing conduit 408, and into the cartomizer 476 of the smoking-substitute device.

The pumping arrangement for this arrangement may be similar (or the same) as the pumping arrangement described in relation to FIGS. 29 to 31.

The port at the remote end 412 of dispensing conduit 408 may comprise a smoking-substitute device coupling assembly 200 or 300, such as those described above (e.g. a coupling assembly as described in relation to FIGS. 6 to 20, or a coupling assembly as described in relation to FIGS. 21 to 28).

In a further optional arrangement, the coupling assembly of the port at the remote end 412 of dispensing conduit 408 may be moveable relative to the end of the dispensing conduit 408. For example, it may be free to move a limited amount into and out of the conduit. Optionally, a biasing element may be provided to act upon the coupling assembly to urge the coupling assembly downwards toward the cartomizer 476 of the smoking-substitute device (when present), to configure the assembly in a dispensing configuration. Further optionally, device receiving port 404 may be configured with a biasing element to act upon the bottom of the cartomizer 476 of the smoking-substitute device to urge the cartomizer 476 of the smoking-substitute device upwards toward the coupling assembly located in the remote end 412 of dispensing conduit 408, to configure the assembly in the dispensing configuration.

Figure 33:
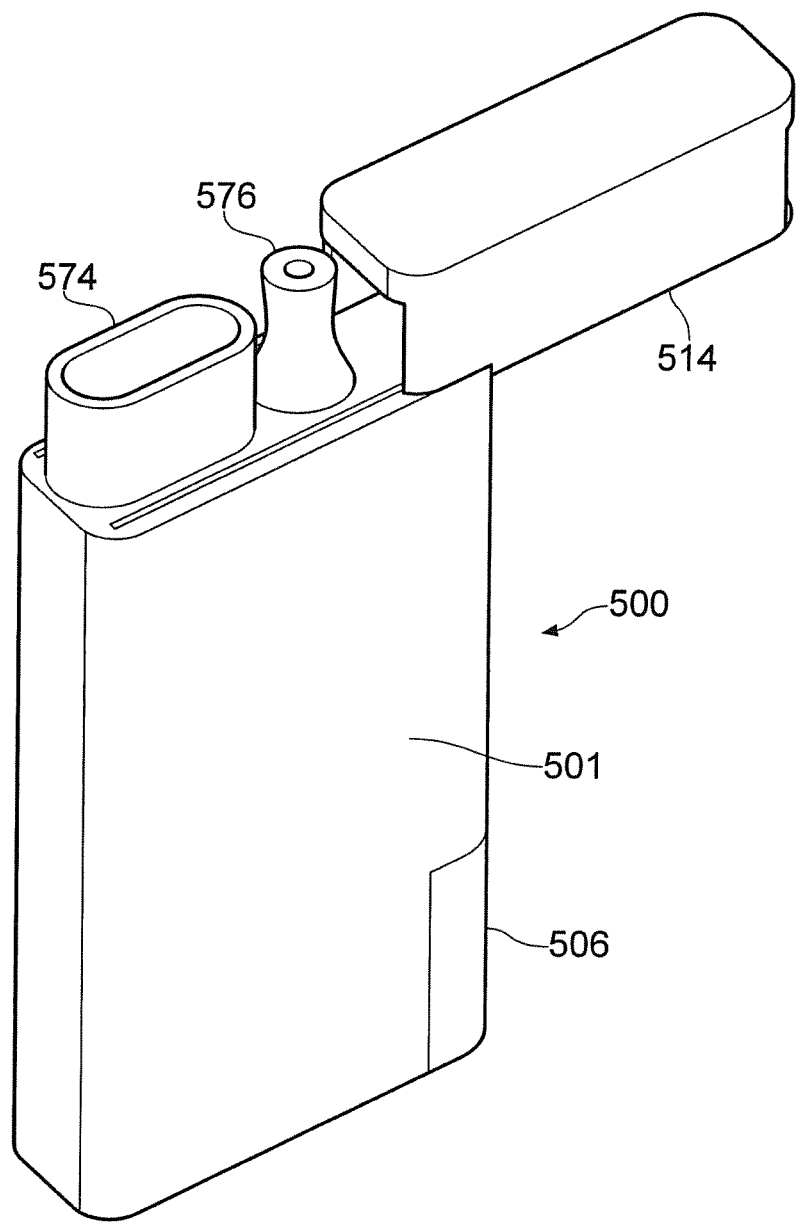
FIG. 33 is a perspective view illustrating a filling apparatus according to a further aspect of the present invention, a dispenser and a cartomizer portion of a smoking-substitute device in a coupled configuration.
Figure 34:
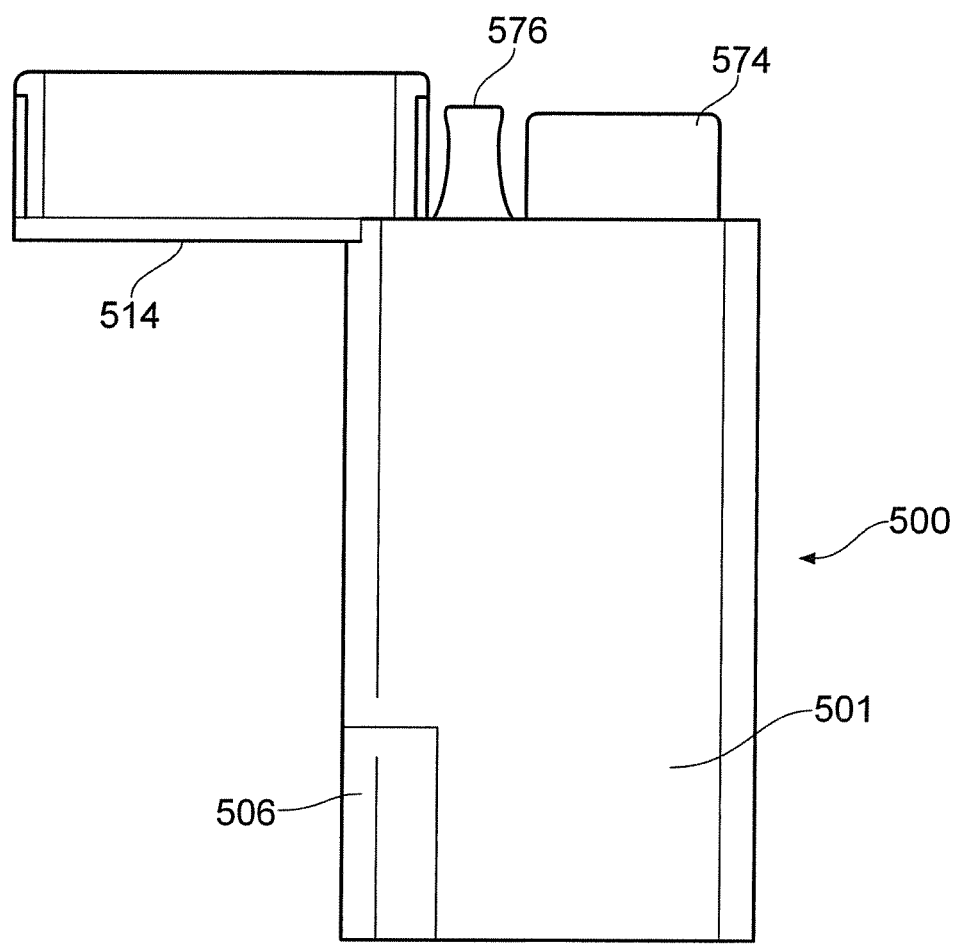
FIG. 34 is a side view illustration of the filling apparatus illustrated in FIG. 30.

FIGS. 33 and 34 show perspective and side views of a filling apparatus 500 which is similar in nature to the filling station apparatus described above in relation to FIGS. 29 to 31. The apparatus 500 is shown in a coupled configuration, i.e. a liquid dispenser bottle 574 and a smoking-substitute device 576 are coupled to the apparatus.

The apparatus 500 comprises a housing 501 in which are formed a dispenser bottle receiving port (not shown) for receiving the liquid dispenser bottle 574 and a smoking-substitute device receiving port (not shown) for the receiving a cartomizer 576 of a smoking-substitute device. An activation button 506 is also provided on the housing 501 for controlling operation of the filling apparatus 500.

Dispenser bottle receiving port is configured to receive a dispensing end of the liquid dispenser bottle 574. Smoking-substitute device receiving port is configured to receive a filling end of the cartomizer 576 of a smoking-substitute device. The dispenser bottle receiving port is in fluid communication with the smoking-substitute device receiving port via a fluid conduit (not shown) located within the housing 501.

The filling station apparatus 500 further comprises a pumping arrangement (not shown) the operation of which is controlled by the activation button 506. In operation, the pumping arrangement serves to exert a pressure on the liquid dispenser bottle 574 located within the dispenser bottle receiving port to expel liquid from the dispenser bottle to the fluid conduit. The pumping arrangement is also operative to cause dispensed liquid to flow through the fluid conduit to the smoking-substitute device receiving port at which point it flows into the cartomizer 576 of a smoking-substitute device located in the smoking-substitute device receiving port.

The filling station apparatus 500 may be suitable for implementing a manual refilling operation of a smoking-substitute device. The dimensions of the filling station apparatus 500 may be such that it is portable (e.g. pocket-sized).

The smoking-substitute device receiving port may comprise a smoking-substitute device engaging portion (e.g. 204 or 302b) of a coupling assembly 200 or 300, such as those described above (e.g. a coupling assembly as described in relation to FIGS. 6 to 20, or a coupling assembly as described in relation to FIGS. 21 to 28). The other end of such coupling assemblies 200, 300, where present, may connect with an end of the fluid conduit within the housing.

In an optional arrangement, the smoking-substitute device receiving port of apparatus 500 may comprise a smoking-substitute device engaging portion of any other suitable type.

The pumping arrangement may be powered by an electrical power source (such as, for example, a battery). In such an arrangement, the activation button 506 may simply be an on/off switch. In an optional arrangement, the pumping arrangement may be mechanically powered via user operation of said the activation button 506. In this optional arrangement, pumping may be achieved by a user pressing the activation button 506 repeatedly. In a yet further optional arrangement, the apparatus 500 may comprise a pumping arrangement which comprises a combination of the above-described electrically and mechanically powered arrangements.

The apparatus 500 further comprises a lid 514 moveable between a first position and a second position. The lid 514 is shown in the first position in FIGS. 33 and 34. In the first position, the dispenser bottle receiving port and the cartomizer receiving port are exposed for access, or, when present, the liquid dispenser bottle 574 and the cartomizer 576 are exposed for access. In the second position, the dispenser bottle receiving port and the cartomizer receiving port are concealed, or, when present, the liquid dispenser bottle 574 and the cartomizer 576 are concealed.

In the illustrated arrangement, the lid 514 comprises a cap slideable relative to one end of the apparatus between the first and second positions. In an optional arrangement, the lid may comprise a hinged cap moveable between the first and second positions.

Figure 35:
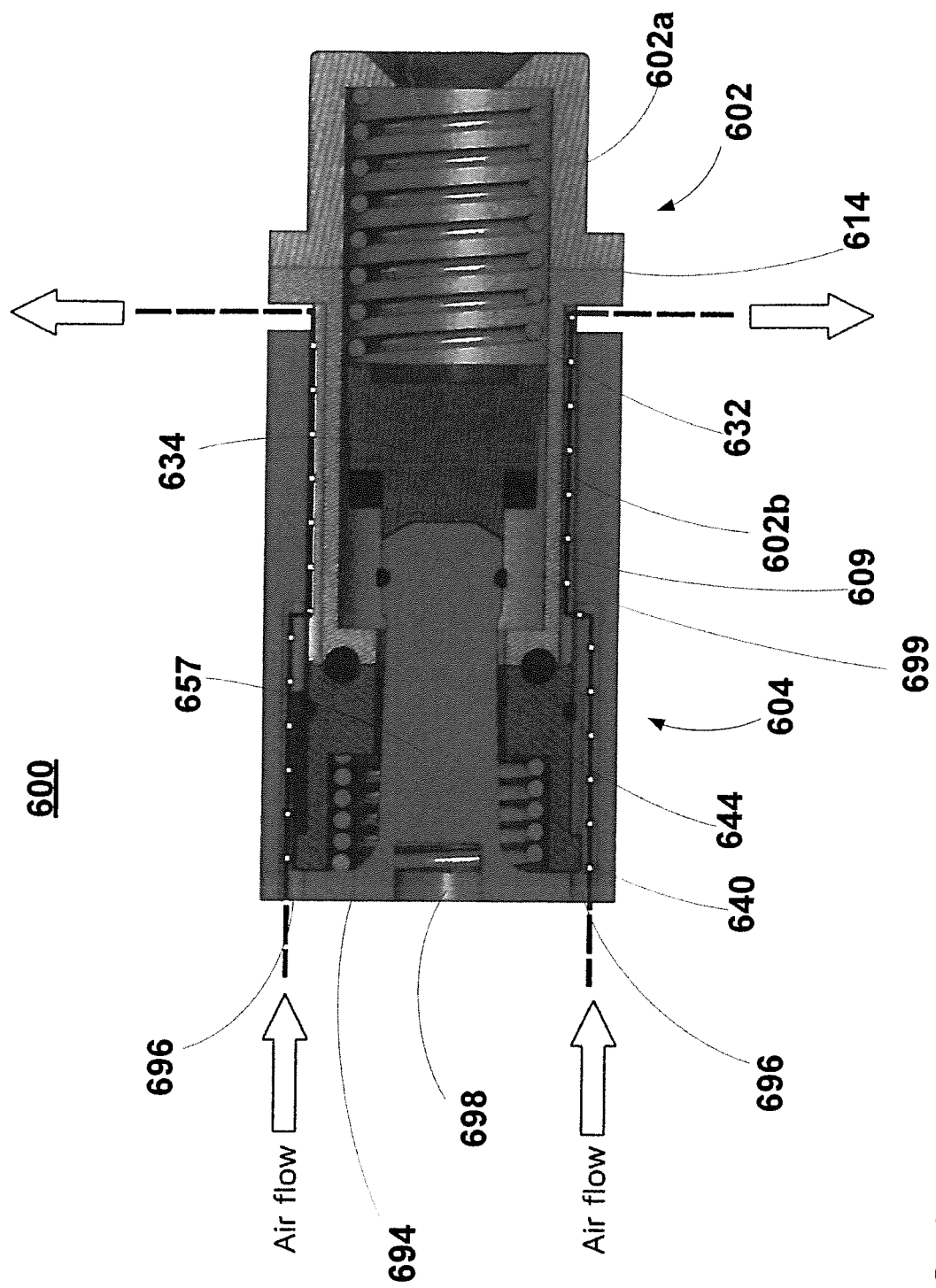
FIG. 35 is cross-sectional side view illustration showing an assembly according to another aspect of the present invention.
Figure 36:
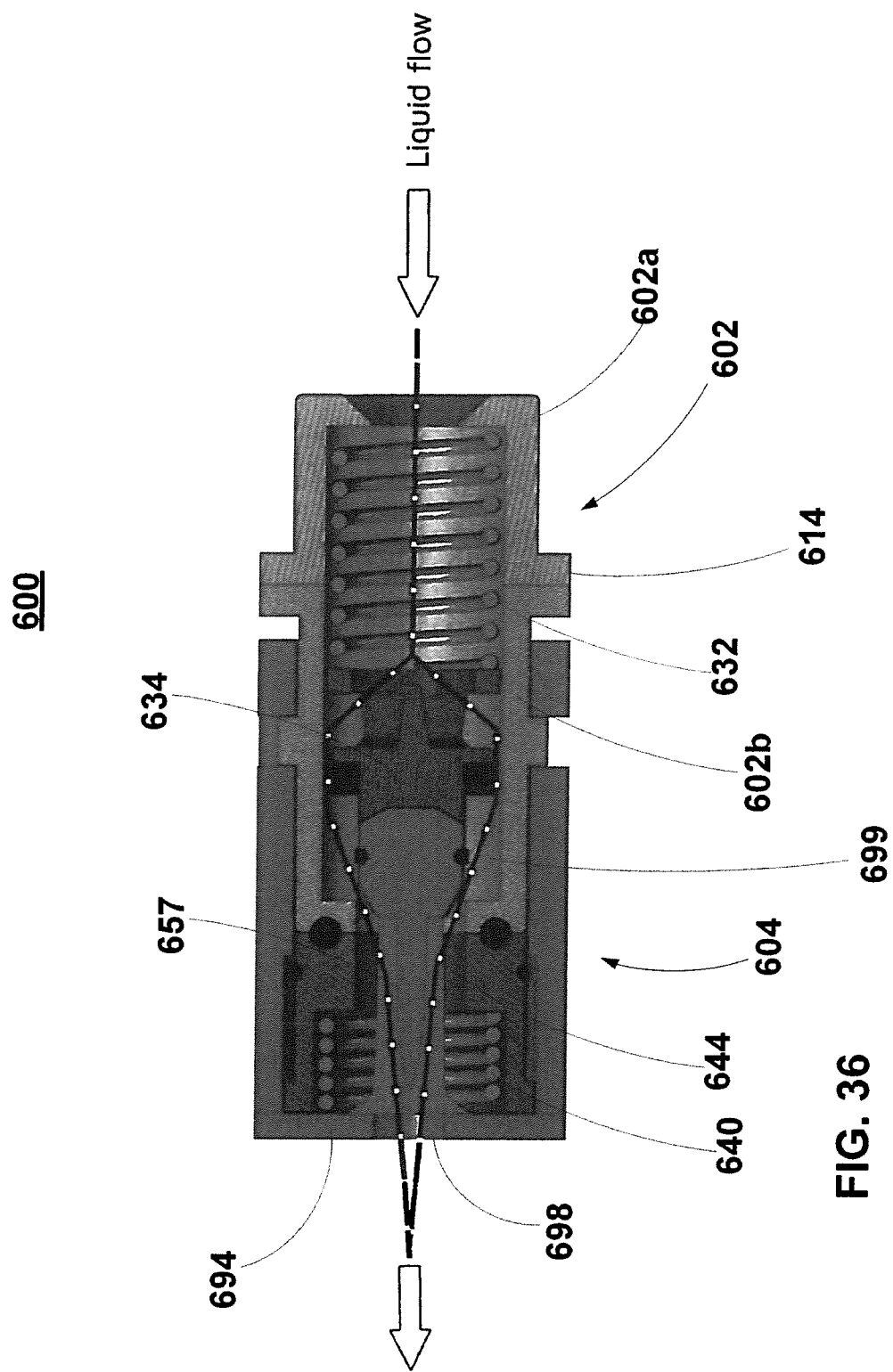
FIG. 36 is a cross-sectional view illustration showing said assembly according to said another aspect of the present invention from a different perspective.
Figure 37:
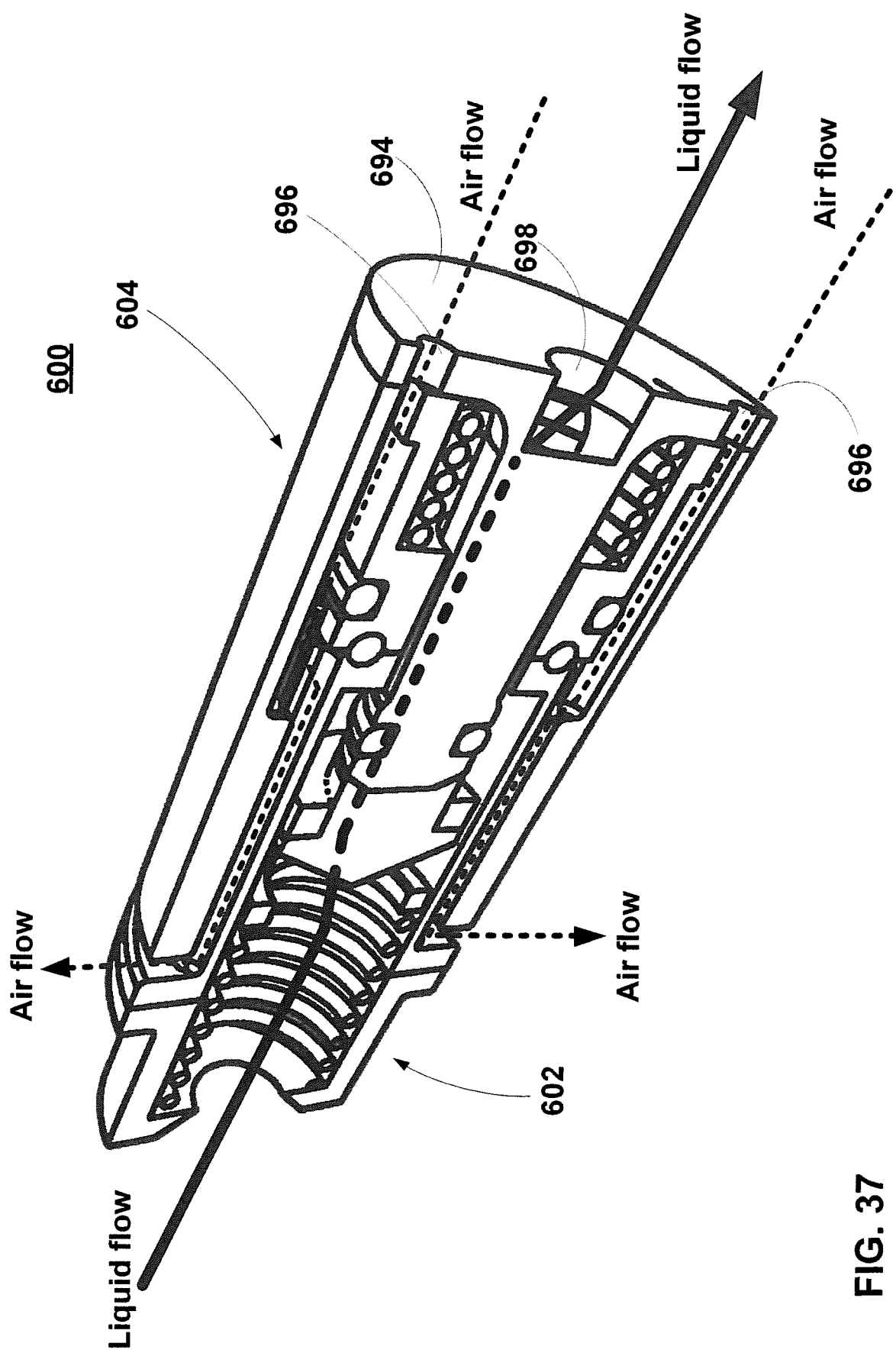
FIG. 37 is a cut-away perspective view illustration showing said assembly according to said another aspect of the present invention from a different perspective.

FIGS. 35 to 37 illustrate an assembly according to another aspect of the present invention.

Features similar to those illustrated in FIGS. 6 to 8, 10 and 13 to 16 are also illustrated in FIGS. 35 to 37. In FIGS. 35 to 37, the features common with those of FIGS. 6 to 8, 10 and 13 to 16 are designated with reference numerals of the type 6XX rather than 2XX.

The assembly 600 is similar to the apparatus 200 described previously and illustrated in FIGS. 6 to 8, 10 and 13 to 16. However, assembly further comprises an end portion 694 to close an end of the female component 604 remote from the end that receives the male component 602.

This end portion 694 comprises at least one aperture 696 to provide fluid communication between an exterior of the female component and grooves 609 of the male component 602. This provides a gas communication pathway through the end portion 694 to the grooves 609 when the female component 604 and male component 602 are engaged. As can be seen in FIG. 35, this can, for example, provide a path for air flow from a reservoir to allow air to be expelled from the reservoir when the reservoir is being filled with liquid from a dispenser.

The end portion 694 also comprises at least one other aperture 698 to provide fluid communication between an exterior of the female component and an interior chamber 699 of the male component 602.

With regard to FIG. 36 which shows a cross-sectional view of the assembly 600 that is orthogonal to that of FIG. 35, this shows the at least one other aperture 698 providing a path for liquid flow from a dispenser, via chamber 699 in male component 602, into a reservoir (not shown) into which the female component 604 is inserted (e.g. when a reservoir is being filled with liquid from a dispenser).

In this aspect of the present invention, the gas and liquid paths through the assembly 600 are physically and/or mechanically separate. Physical and/or mechanical separation of gas and liquid communication pathways in the assembly may allow an ambient pressure to be maintained in a reservoir being filled using the assembly. Further, leakage of liquid from the liquid communication pathway to the gas communication pathway may be inhibited.

FIG. 37 illustrates a cut-away perspective view of the assembly 600 of FIGS. 35 and 36 to show the separate liquid and gas paths through the assembly.

There has been described in the foregoing one or more embodiments of a smoking-substitute device and refilling apparatus for a substitute-smoking device that avoids or at least ameliorates the problems of the prior art and that addresses the statutory legal requirements that will shortly be implemented in certain markets. More particularly, there is disclosed one or more embodiments of a smoking-substitute device and smoking-substitute device refill apparatus that permits the refilling of a reservoir from a dispenser without, or at least with reduced, leakage or spillage.

As used herein any reference to "one embodiment" or "an embodiment" means that a particular element, feature, structure, or characteristic described in connection with the embodiment is included in at least one embodiment. The appearances of the phrase "in one embodiment" or the phrase "in an embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

In view of the foregoing description it will be evident to a person skilled in the art that various modifications may be made within the scope of the invention. For example, although helical coil springs have been described in the foregoing, embodiments in accordance with the present invention are not limited to using such springs. Other resiliently biased structures may be used such as leaf springs or a resiliently compressible or extendable material. Different configurations of resilient member may be used for respective male and female elements. Additionally, slots 220 need not extend precisely circumferentially but merely transverse to the direction of insertion of the male component into the female component such that movement in the insertion direction is inhibited.

In the described embodiment, helical coil spring 232 has an end distal from the plunger abutting an interior formation 231 of the end cap 230. Optionally, that end of spring 232 may abut the end wall of end cap 230.

The scope of the present disclosure includes any novel feature or combination of features disclosed therein either explicitly or implicitly or any generalisation thereof irrespective of whether or not it relates to the claimed invention or mitigate against any or all of the problems addressed by the present invention. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

Yet further aspects and embodiments of the invention are enumerated with reference to the following numbered clauses.

1. A system for transferring liquid between a dispenser and a reservoir comprising:
   a coupling assembly for securably and sealably engaging said dispenser to said reservoir, said assembly moveable between an unsecured and closed position in which liquid and gas communication is restricted between a dispenser outlet and a reservoir inlet and a reservoir outlet and a dispenser inlet, and a secured and open position in which said assembly opens a liquid communication pathway between said dispenser and said reservoir through the dispenser outlet and reservoir inlet.
2. The system according to clause 1, wherein said assembly opens a gas communication pathway between said reservoir and said dispenser through said reservoir outlet and dispenser inlet.
3. The system according to clause 1 or 2, wherein said assembly opens a gas communication pathway between said reservoir and atmosphere through said reservoir outlet and a vent in said system.
4. The system according to clauses 1, 2 or 3, wherein the coupling assembly is adapted to close both the liquid communication pathway and the gas communication pathway as it is moved away from the secured position to disengage the dispenser and reservoir.
5. The system according to any of the preceding clauses, wherein, in the open position, the system is operable to permit liquid to be transferred through the liquid communication pathway, and for a substantially equivalent volume of gas to be expelled through the gas communication pathway.
6. The system according to clause 5, wherein, in the open position, the system is adapted to maintain a substantially equal pressure in the dispenser and reservoir.
7. The system according to any of the preceding clauses, wherein said dispenser outlet comprises a valve that is actuable when the engagement means is secured in the open position to open said liquid communication pathway between said dispenser and said reservoir.
8. The system according to any of the preceding clauses, wherein said reservoir outlet comprises a valve that is actuable when the engagement means is secured in the open position to open said gas communication pathway between said reservoir and dispenser.
9. The system according to clause 8, wherein the valve is biased to close the gas communication pathway when the coupling assembly is not secured in the open position.
10. The system according to any of the preceding clauses, wherein the coupling assembly comprises a guide assembly for guiding movement of the dispenser outlet into the secured and open position.
11. The system according to any of the preceding clauses, wherein the coupling assembly comprises a male member, and a female member configured for securely and removably receiving said male member.
12. The system according to any of the preceding clauses, wherein the coupling assembly comprises a bayonet-type arrangement.
13. The system according to any of the preceding clauses, wherein the coupling assembly comprises a magnetic-type arrangement.
14. The system according to any of the preceding clauses, wherein the coupling assembly comprises a screw-type arrangement.
15. The system according to any of the preceding clauses, wherein the coupling assembly comprises a slide-type arrangement.
16. The system according to any of the preceding clauses, wherein the coupling assembly comprises a friction-fit-type arrangement.
17. The system according to any of the preceding clauses, wherein the coupling assembly comprises a speed-fit type arrangement.
18. A coupling assembly configured to cooperate with and be operative in the system of any preceding clause.
19. A dispenser configured to cooperate with and be operative in the system of any of clauses 1 to 17.
20. A reservoir configured to cooperate with and be operative in the system of any of clauses 1 to 17.
21. An assembly for transferring liquid between a dispenser and a reservoir, said assembly comprising:
    a first portion configured for sealably cooperating with a mutually cooperative formation of said reservoir;

a second portion connected to said first portion and configured for sealably cooperating with a mutually cooperative formation of said dispenser; and a chamber formed within said first and second portions, and including a first aperture at an end of said first portion and a second aperture at an end of said second portion;

wherein said assembly is configurable between:

a non-dispensing configuration in which liquid communication between said chamber and said first aperture is restricted; and a dispensing configuration in which a liquid communication pathway is opened between the chamber and said first aperture to communicate liquid between said dispenser and said reservoir through a dispenser outlet and reservoir inlet, and a gas communication pathway is formed between a formation on a body of said first portion and a formation of said reservoir for expulsion of gas from said reservoir; and further wherein alternation between said non-dispensing configuration and said dispensing configuration is effected responsive to application of an actuation force, exerted via an actuation formation of said reservoir, to a closure member located within said chamber.

22. The assembly according to clause 23, wherein the assembly is configure to close the liquid communication pathway responsive to removal of said actuation force.

23. The assembly according to clause 23 or 24, wherein, in the dispensing configuration, the assembly is operable to permit liquid to be transferred through the liquid communication pathway, and for a substantially equivalent volume of gas to be expelled from said reservoir via said gas communication pathway.

24. The assembly according to any one of clauses 23 to 25, wherein said closure member is biased to close the liquid communication pathway in the absence of said actuation force.

25. The assembly according to any one of clauses 23 to 26, wherein said first portion comprises a male member configured to be received in a mutually complementary female member of said reservoir.

26. The assembly according to any one of clauses 23 to 27, wherein said second portion comprises a male member configured to be received in a mutually complementary female member of said dispenser.

27. The assembly according to any one of clauses 23 to 28, configured for sealably cooperating with a reservoir of a smoking-substitute device, and optionally securably cooperating with the reservoir of a smoking-substitute device.

28. The assembly according to clause 29, wherein said first aperture is configured to receive therethrough a gas passageway of said smoking-substitute device, said gas passageway comprising said actuation formation of said reservoir.

29. The assembly according to clause 30, wherein a portion of said liquid communication pathway is formed between said first aperture and said gas passageway.

30. The assembly according to clause 30 or 31, wherein said closure member is configured to sealably close said gas passageway responsive to application of said actuation force.

31. A dispenser configured to cooperate with and be operative with the assembly of any one of clauses 23 to 32.

32. A reservoir configured to cooperate with and be operative with the assembly of any one of clauses 23 to 32.

33. A system for transferring liquid between a dispenser and a reservoir, comprising: an assembly according to any one of clauses 23 to 32; a dispenser according to clause 33; and a reservoir according to clause 34.

34. A filling station for transferring liquid between a dispenser and a reservoir, comprising: a housing; a first coupling point formed in said housing, said first coupling point for sealably cooperating with said dispenser; a second coupling point formed in said housing, said second coupling point configured for sealably cooperating with a mutually cooperative formation of said reservoir; a conduit located in said housing and providing fluid communication between said first coupling point and said second coupling point.

35. The filling station according to clause 36, further comprising a pump operative to pump liquid from said dispenser to said reservoir via said conduit; and a user operable actuator to control operation of said pump.

36. The filling station according to clause 36 or 37, wherein said first and/or said second coupling point is further configured for securably engaging said reservoir.

37. The filling station according to any one of clauses 36 to 38, wherein said second coupling point comprises an assembly according to any one of clauses 23 to 32.

38. The filling station according to clause 39, wherein said second portion of said assembly is in fluid communication with one end of said conduit.

39. The filling station according to clause 39 or 40, further comprising a biasing element for urging said reservoir toward said second coupling point, or vice versa, to configure said assembly in said dispensing configuration.

40. The filling station according to any one of clauses 36 to 41, wherein said pump is electrically powered from a power source.

41. The filling station according to any one of clauses 36 to 41, wherein said pump is mechanically powered via user operation of said user operable actuator.

42. A smoking-substitute device comprising a reservoir according to clause 34.

43. The smoking-substitute device according to clause 44, wherein said reservoir is removable from the device.

44. The smoking-substitute device according to clause 44, wherein the reservoir is integral with the device.

The invention claimed is:

1. An assembly for controllably transferring liquid therethrough, said assembly comprising:

a reservoir portion configured for securely coupling to a liquid reservoir inlet; and a dispenser portion connected to said reservoir portion and configured for securely coupling to a liquid dispenser outlet;

wherein said reservoir portion and dispenser portion configured to cooperatively combine to form said liquid communication pathway;

wherein said assembly is moveable between an unsecured and closed configuration in which liquid communication is restricted between a first aperture disposed at an end of the dispenser portion and a second aperture disposed at an end of the reservoir portion, and a secured and open configuration in which a liquid communication pathway between said first and said second aperture is opened; wherein said assembly is configured to provide a gas communication pathway through said assembly for venting gas from the reservoir portion an exterior of said assembly responsive to movement of said assembly to said secured and open configuration, said assembly configured to close said gas communication pathway in said unsecured and closed configuration; and wherein the gas communication pathway is configured to inhibit the passage of a liquid therethrough.

2. The assembly according to claim 1, wherein said gas communication pathway is configured to vent gas to the exterior of said assembly concomitant with movement of said assembly between said closed and said open configurations.

3. The assembly according to claim 1, wherein said gas communication pathway is configured to vent to atmosphere.

4. The assembly of claim 1, wherein the gas communication pathway is configured to inhibit capillary motion of a liquid from a reservoir through the gas communication pathway.

5. The assembly of claim 1, wherein the gas communication pathway comprises one or more convolutions.

6. The assembly according to claim 1, wherein the assembly is configured to close both the liquid communication pathway and the gas communication pathway responsive to movement away from the secured position.

7. The assembly according to claim 1, wherein, in the open configuration, the assembly is operable to permit liquid to be transferred through the liquid communication pathway, and for a substantially equivalent volume of gas to be expelled through the gas communication pathway.

8. The assembly of claim 1, wherein the assembly is biased towards the closed configuration.

9. The assembly according to claim 8, wherein a bias of said assembly towards the closed configuration is a resilient bias.

10. The assembly according to claim 1, comprising a first valve arrangement for opening and closing said liquid communication pathway and a second valve arrangement operatively coupled to said first valve arrangement to open and close said gas communication pathway responsive to said movement of said assembly to said secured and open configuration.

11. The assembly according to claim 10, wherein the first and second valve arrangements are biased shut when the assembly is not secured in the open configuration.

12. The assembly according to claim 1, wherein said reservoir portion comprises a first closure member and said dispenser portion comprises a second closure member for closing said liquid communication pathway, said first and second closure members seated in respective first and second closeable apertures in the unsecured and closed configuration and movable to the secured and open configuration to open said liquid communications pathway.

13. The assembly according to claim 12, wherein said first closure member and said second closure member are configured to abut one another to effect movement of said first and second closure members from said first and second closeable apertures responsive to an actuation force applied to a one or more of said first and second closure members.

14. The assembly according to claim 1, wherein, said reservoir portion comprises first and second components configured to cooperatively define a gas channel open at an end proximal said first aperture and extending to an end distal said first aperture, said first and second components movable with respect to each other to open said distal end of said gas channel; and said dispenser portion comprises a third component movable with respect to the first component to act on said second component to move said first and second components with respect to each other concomitant with movement of said assembly from a non-dispensing configuration to a dispensing configuration to expose said distal end of said gas channel to provide said gas communication pathway to the exterior of said assembly.

15. The assembly of claim 14, wherein said third component is configured to provide a second gas channel including an end configured to open to the distal end of said gas channel to provide said gas communication pathway to the exterior of said assembly responsive to movement of said first and second component with respect to each other under actuation of said third component.

16. The assembly of claim 15, wherein an inner wall of said second component and an outer wall of said third component are configured to cooperate to provide said second gas channel.

17. The assembly of claim 16, wherein said outer wall of said third component comprises a groove extending lengthwise from an end region of said third component distal said second aperture.

18. The assembly of claim 17 wherein said reservoir portion and said dispenser portion cooperate to form another groove between the inner wall of said first component and the outer wall of said second component to provide said gas channel.

19. The assembly according to claim 1, further comprising mutually complementary interengagement formations disposed on said reservoir portion and said dispenser portion and configured to securely engage said reservoir portion to said dispenser portion in said secured and open configuration.

20. The assembly according to claim 19, wherein said reservoir portion comprises a first closure member and said dispenser portion comprises a second closure member for closing said liquid communication pathway, and wherein said mutually complementary interengagement formations are configured to guide movement of the reservoir portion and the dispenser portion with respect to each other to move said first and second closure members from said unsecured and closed configuration to said secured and open configuration.

21. The assembly according to claim 12, wherein said first closure and first closeable aperture and said second closure and said second closeable aperture form said first valve arrangement.

22. The assembly according to claim 14, wherein said gas channel and said second gas channel form said second valve arrangement.

* * * * *

UNITED STATES PATENT AND TRADEMARK OFFICE
CERTIFICATE OF CORRECTION

PATENT NO. : 10,865,095 B2
APPLICATION NO. : 15/550726
DATED : December 15, 2020
INVENTOR(S) : Kenneth Scott et al.

It is certified that error appears in the above-identified patent and that said Letters Patent is hereby corrected as shown below:

On the Title Page

Item (30), should read as follows:
--(30) Foreign Application Priority Data
Feb. 13, 2015 (GB)...................1502492.0
Mar. 26, 2015 (GB)...................1505216.0
Jan. 20, 2016 (GB)...................1601096.9--

Signed and Sealed this
Third Day of May, 2022

Katherine Kelly Vidal
*Director of the United States Patent and Trademark Office*